US006537545B1

(12) United States Patent
Karageozian et al.

(10) Patent No.: US 6,537,545 B1
(45) Date of Patent: Mar. 25, 2003

(54) USE OF CORNEAL HARDENING AGENTS IN ENZYMEORTHOKERATOLOGY

(75) Inventors: Hamper Karageozian, San Juan Capistrano, CA (US); John Y. Park, Santa Ana, CA (US); Vicken Karageozian, San Juan Capistrano, CA (US); Phillip Baker, Walnut Creek, CA (US); Anthony Nesburn, Malibu, CA (US)

(73) Assignee: ISTA Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 09/656,849

(22) Filed: Sep. 7, 2000

Related U.S. Application Data

(63) Continuation of application No. PCT/US99/05135, filed on Mar. 9, 1999
(60) Provisional application No. 60/077,339, filed on Mar. 9, 1998.

(51) Int. Cl.[7] ................................................ A61K 38/44
(52) U.S. Cl. .................. 424/94.4; 424/94.2; 424/94.62; 424/429; 424/427; 424/78.04
(58) Field of Search .................................. 424/422, 427, 424/429, 94.1, 94.2, 94.3, 94.62, 94.4, 78.04; 435/201, 183

(56) References Cited

U.S. PATENT DOCUMENTS

| | | | |
|---|---|---|---|
| 3,728,223 A | 4/1973 | Kaneko et al. |
| 3,760,807 A | 9/1973 | Neefe |
| 3,945,889 A | 3/1976 | Mima et al. |
| 4,258,134 A | 3/1981 | Yoshida et al. |
| 4,881,543 A | 11/1989 | Trembly et al. |
| 4,897,349 A | 1/1990 | Swann et al. |
| 4,904,594 A | 2/1990 | Karlstam |
| 5,061,627 A | 10/1991 | Olsen et al. |
| 5,270,051 A | 12/1993 | Harris |
| 5,316,926 A | 5/1994 | Brown et al. |
| 5,496,726 A | 3/1996 | Park et al. |
| 5,593,877 A | 1/1997 | King |
| 5,626,865 A | 5/1997 | Harris et al. |
| 5,695,509 A | 12/1997 | El Hage |
| 5,747,027 A | 5/1998 | Stern et al. |
| 5,756,552 A | 5/1998 | Takeuchi et al. |
| 5,779,696 A | 7/1998 | Berry et al. |
| 5,788,957 A | 8/1998 | Harris |
| 5,827,721 A | 10/1998 | Stern et al. |
| 5,866,120 A | 2/1999 | Karageozian et al. |
| 6,039,943 A | 3/2000 | Karageozian et al. |
| 6,123,938 A | 9/2000 | Stern et al. |
| 6,132,735 A | 10/2000 | Harris et al. |
| 6,161,544 A | 12/2000 | DeVore et al. |
| RE37,336 E | 8/2001 | Weigel et al. |

FOREIGN PATENT DOCUMENTS

| | | |
|---|---|---|
| EP | 0 367 514 | 10/1989 |
| EP | 0625579 B1 | 11/1994 |
| EP | 1048725 A1 | 11/2000 |
| GB | 1 382 015 | 6/1973 |
| WO | 93/07840 | 4/1993 |
| WO | 97/18835 | 5/1997 |
| WO | 98/52602 | 11/1998 |
| WO | 99/39238 | 8/1999 |
| WO | WO 0077221 | 12/2000 |

OTHER PUBLICATIONS

Benson, et al. (1971) *Vitreous Hemorrhage.* Survey of Ophthalmology 5:297–311.
Boyer, et al. (1958) *Studies on Simulated Virteous Hemorrhages.* A.M.A. Archives of Ophthalmology 59:333–336.
Harooni, et al. (1998) *Efficacy and Safety of Enzymatic Posterior Vitreous Detachment by Intravitreal Injection of Hyaluronidase.* Retina 18:116–22.
Harooni, et al. (1996) *Efficacy and Safety of Vitreous Liquefaction by Intravitreal Injection of Hyaluronidase.* Abstract: Investigative Ophthalmology and Visual Science, Annual Meeting Fort Lauderdale, FL. 4–21 through 4–26–96.
Kang, et al. (1995) *Induction of Bitreolysis and Vitreous Detachment with Hyaluronidase and Perfluoroproopane Gas.* Korean J. Ophthalmol. 9:69–78.
Knepper, et al. (1984) *Exogenous Hyaluronidases and Degradation of Hyaluronic Acid in the Rabbit Eye.* Investigative Ophthalmology & Visual Science 25:286–293.
LaNauze, et al. (1982) *Chemotaxis in Vitreous Hemorrhage: An Experimental Study.* Exp. Eye Res. 34:803–813.
Maberley, et al. (1970) *The Effect of a Fibrinolytic Agent on Vitreous Hemorrhage in Rabbits.* Canad. J. Ophthal. 5:55–63.
Pirie (1949) *The Effect of Hyaluronidase Injection on The Vitreous Humour of the Rabbit.* British J. Ophthal. 1949:678–684.
Regnault (1970) *Vitreous Hemorrhage: An Experimental Study.* Arch. Ophthal. 83:458–465.

(List continued on next page.)

Primary Examiner—Leon B. Lankford, Jr.
Assistant Examiner—Ruth A. Davis
(74) Attorney, Agent, or Firm—Knobbe Martens Olson & Bear LLP

(57) ABSTRACT

An Enzyme Orthokeratology method is provided for correcting refractive errors in the eye of a subject mammal. Accelerating reshaping of the cornea is accomplished by administering a corneal hardening amount of a corneal hardening agent to the eye of the subject. Reformation is accomplished under the influence of a rigid contact lens or a series of lenses having a concave curvature that will correct a refractive error. The cornea rapidly reshapes its convex curvature to the concave curvature of the contact lens, rendering the eye emmetropic. The cornea is permitted to "harden" to retain the new emmetropic shape. After "hardening" has occurred, the lens rendering the eye emmetropic is removed.

8 Claims, 5 Drawing Sheets

OTHER PUBLICATIONS

Schimek, et al. (1954) *Vitreous Hemorrhage Absorption—Experimental Study on Rabbit Eyes of the Effects of Intravitreal Hyaluronidase and Streptokinase—Streptodornase and on the Influence of ACTH and Cortisone.* Arch. Ophthal. 82:677–683.

Skrzypczak–Spak, et al. (1971) *Experimental Liquefaction of the Vitreous Body.* Annals of Ophthalmology 3(6):624–630.

Stern, et al. (1992) *An ELISA–Like Assay for Hyaluronidase and Hyaluronidase Inhibitors.* Matrix 12:397–403.

Tanaka, et al. (1996) *Efficacy of Hyaluronidase to Liquefy Vitreous and to Facilitate the Clearance of Vitreous Hemorrhage.*

Treister, et al. (1969) *The Effect of Subconjunctivally Injected Hyaluronidase on Corneal Refraction.* Arch Ophthal. 81:645–649.

Twining, et al. (1984) *Acid Proteases of Vitreal Macrophages.* 3(8):1055–1062.

Vercruysse, et al. (1994) *Kinetic Investigation of the Degradation of Hyaluronan by Hyaluronidase using gel Permeation Chromatography.* J. Chromatogr. B 656:179–190.

TABLE II
50 IU Hyaluronidase Injection, Corrective Lenses and 3% Glyceraldehyde Solution

| Subject | Tx. Group | Baseline | End RL+ Glycer- aldehyde | UNCORRECTED VISUAL ACUITY (Snellen/ETDRS) | | | | | | |
|---|---|---|---|---|---|---|---|---|---|---|
| | | | | 1-Week Follow- up | 2-Week Follow- up | 3-Week Follow- up | 1-Month Follow- up | 2-Month Follow- up | 3-Month Follow- up | 4-Month Follow- up | 5-Month Follow- up |
| ARR/001 | 50 IU | 20/80 | 20/25 | 20/40 | 20/30 | 20/40 | 20/50 | 20/30 | 20/60 | N/D | 20/50 20/40 |
| JCV/002 | 50 IU | 20/300 | 20/20 | 20/30 | 20/50 | 20/50 | N/D | 20/120 | 20/160 | 20/125 | |
| SRA/007 | 50 IU | 20/200 | 20/20 | 20/40 | 20/40 | 20/40 | 20/40 | 20/80 | 20/50 | — | |
| FAH/009 | 50 IU | 20/200 | 20/20 | 20/50 | 20/40 | 20/120 | 20/80 | 20/60 | 20/63 | | |
| JRF/010R | 50 IU | 20/80 | 20/20* | 20/20 | 20/20 | N/D | 20/20 | Not Yet obtained | Not Yet obtained | | |
| JLV/015 | 50 IU | 20/80 | 20/40 | 20/30 | 20/25 | 20/50 | N/D | 20/40 | 20/25 | | |
| OCS/022R | 50 IU | 20/63 | N/D | 20/50 | N/D | 20/80 | Not Yet obtained | Not Yet obtained | Not Yet obtained | | |
| JLM/024R | 50 IU | 20/100 | N/D | N/D | N/D | 20/50 | 20/40 | Not Yet obtained | Not Yet obtained | | |
| LMR/028 | 50 IU | 20/300 | 20/20 | 20/120 | N/D | 20/100 | 20/100 | 20/125 | Not Yet obtained | | |
| GJM/029 | 50 IU | 20/200 | 20/20 | N/D | 20/30 | 20/30 | 20/32 | 20/40 | Not Yet obtained | | |
| ECF/033 | 50 IU | 20/300 | 20/20 | 20/200 | 20/200 | N/D | 20/125 | 20/125 | Not Yet obtained | | |

*-unscheduled visit: UCVA = 20/80 (Snellen),20/80 (ETDRS)
-PROTOCOL DEVIATION: Subject had not been compliant with study treatment over past week-lens re-fitted, treatment extended for one more week
SRA/007 -forming lens started 21 days post-injection
JRF-010R* 
OCS/022R -forming lens started 21 days post-injection
JLM/024R

FIG.2

TABLE IIIA

500 IU Hyaluronidase Injection, Corrective Lenses and 3% Glyceraldehyde Solution UNCORRECTED VISUAL ACUITY (Snellen/ETDRS)

| Subject | Tx. Group | Baseline | End RL+ Glyceraldehyde | 1-Week Follow-up | 2-Week Follow-up | 3-Week Follow-up | 1-Month Follow-up | 2-Month Follow-up | 3-Month Follow-up | 4-Month Follow-up |
|---|---|---|---|---|---|---|---|---|---|---|
| ECS/004 | 500 IU | 20/160 | 20/20 | 20/60 | 20/50 | 20/50 | 20/30 | 20/32 | 20/60 | 20/50 |
| PIQ/008 | 500 IU | 20/400 | 20/16 | N/D | 20/50 | 20/60 | N/D | N/D | 20/80 | |
| YAM/013 | 500 IU | 20/100 | 20/40 | 20/32 | 20/25 | 20/20 | 20/20 | 20/30 | 20/40 | |
| YOC/017 | 500 IU | 20/50 | N/D | N/D | N/D | N/D | 20/25 | 20/20 | 20/25 | |
| FGM/018 | 500 IU | 20/80 | 20/20 | 20/25 | 20/20 | 20/20 | 20/20 | 20/20 | 20/25 | |
| JPG/019 | 500 IU | 20/70 | 20/12.5 | N/D | 20/20 | 20/20 | 20/20 | 20/25 | 20/15 | |
| ESS/020 | 500 IU | 20/500 | 20/20 | 20/50 | 20/50 | 20/40 | 20/50 | 20/63 | Not Yet obtained | |
| FMP/023 | 500 IU | 20/70 | 20/20 | 20/25 | 20/15 | 20/20 | 20/20 | 20/20 | Not Yet obtained | |
| ERG/026 | 500 IU | 20/50 | 20/20 | 20/20 | 20/20 | N/D | 20/20* | 20/25 | Not Yet obtained | |
| ELG/030 | 500 IU | 20/300 | 20/16 | 20/200 | N/D | 20/160 | 20/200 | 20/100 | Not Yet obtained | |
| OOS/031 | 500 IU | 20/200 | 20/16 | 20/50 | 20/60 | N/D | 20/60 | 20/50 | 20/50 | |

YAM/013 —seen 40 days after RL/G: UCVA 20/20 (20/20)
FGM/018 —unscheduled visit 50 days – UCVA – 20/20 (Snellen) 20/20 (ETDRS)
JPG/019 —missed 1 month follow up visit; seen 42 days after D/C RL/G) – UCVA 20/20
ESS/020 —42 day follow up
ERG/026* —unscheduled visit, 35 day follow up – UCVA – 20/20 (Snellen) 20/20⁻¹ (ETDRS)

FIG.3

TABLE IIIB

500 IU Hyaluronidase Injection, Corrective Lenses and 3% Glyceraldehyde Solution

| Subject | Tx. Group | UNCORRECTED VISUAL ACUITY (Snellen/ETDRS) | | | | | | | |
|---|---|---|---|---|---|---|---|---|---|
| | | Baseline | End RL+ Glyceraldehyde | 1-Week Follow-up | 2-Week Follow-up | 3-Week Follow-up | 1-Month Follow-up | 2-Month Follow-up | 3-Month Follow-up |
| NMD/101 | 500 IU (Gr.VI) | 20/200 | 20/25 | 20/80 | 20/100 | 20/80 | 20/60 | Not Yet obtained | Not Yet obtained |
| AVM/102 | 500 IU (Gr.VI) | 20/160 | 20/15 | 20/25 | 20/20 | 20/15 | 20/20 | 20/20 | Not Yet obtained |
| LLG/103 | 500 IU (Gr.VI) | 20/160 | 20/15 | 20/60 | 20/80 | 20/50 | 20/50 | 20/50 | Not Yet obtained |
| LMR/104 | 500 IU (Gr.VI) | 20/400 | 20/50 | 20/80 | 20/60 | 20/30 | 20/80 | Not Yet obtained | Not Yet obtained |
| IEV/105 | 500 IU (Gr.VI) | 20/200 | 20/20 | N/D | 20/80 | N/D | N/D | 20/80 | Not Yet obtained |
| GVC/106 | 500 IU (Gr.VI) | 20/160 | 20/20 | 20/80 | 20/80 | 20/25 | 20/50 | 20/63 | Not Yet obtained |
| MCS/107 | 500 IU (Gr.VI) | 20/60 | 20/20 | 20/80 | 20/20 | 20/25 | 20/20 | Not Yet obtained | Not Yet obtained |

FIG.4

TABLE IV
Corrective Lenses and 3% Glyceraldehyde Solution

| Subject | Tx. Group | Baseline | End RL + Glyceraldehyde | UNCORRECTED VISUAL ACUITY (Snellen/ETDRS) ||||||| 
|---|---|---|---|---|---|---|---|---|---|---|
| | | | | 1-Week Follow-up | 2-Week Follow-up | 3-Week Follow-up | 1-Month Follow-up | 2-Month Follow-up | 3-Month Follow-up | 4-Month Follow-up | 5-Month Follow-up |
| ESV/005 | No. Enz. | 20/100 | 20/20 | 20/40 | 20/63 | 20/63 | 20/63 | 20/125$^v$ | 20/200 | 20/100 | |
| GVC/006 | No. Enz. | 20/200 | | NOT AVAILABLE | | | | | 20/160 | N/D | 20/100 |
| SGS/011 | No. Enz. | 20/200 | 20/12.5 | 20/32 | 20/40 | 20/20 | 20/32 | 20/32 | 20/40 | | |
| JAM/012 | No. Enz. | 20/200 | 20/16 | 20/60 | N/D | N/D | N/D* | 20/80 | 20/120 | 20/100 | |
| AJG/014 | No. Enz. | 20/80 | 20/20 | 20/25 | 20/25 | 20/30 | N/D | 20/32 | 20/50 | | |
| MCS/016 | No. Enz. | 20/300 | | NOT AVAILABLE | | | | 20/80 | 20/60 | 20/80 | |
| ERR/021 | No. Enz. | 20/80 | 20/15 | 20/100 | N/D | N/D | 20/40$^v$ | 20/60 | Not Yet obtained | | |
| ARP/032 | No. Enz. | 20/120 | 20/100 | 20/30 | 20/100 | 20/120 | 20/63 | 20/60 | Not Yet obtained | | |

ESV/005$^\sim$ –Unscheduled visit on 69 days follow up – UCVA = 15/80 (Snellen), 20/80$^{-1}$ (ETDRS).
JAM/012* –Unscheduled visit on day 49 follow up – UCVA = 20/120 (Snellen), 20/125$^{-2}$ (ETDRS)
AJG/012 –Unscheduled visit on 6 week follow up – UCVA = 20/40 (Snellen), 20/32$^{-2}$ (ETDRS)
ERR/021$^v$ –Unscheduled visit on 35 days post RL/G – UCVA = 20/60 (Snellen), 20/63 (ETDRS)

FIG.5

USE OF CORNEAL HARDENING AGENTS IN ENZYMEORTHOKERATOLOGY

RELATED APPLICATIONS

This application is a continuation which claims the benefit of priority of Intl Pat Appl No PCT/US99/05135 filed Mar. 9, 1999, designating the United States of America and published in English, which claims the benefit of priority of U.S. Pat Appl No 60/077,339, filed Mar. 9, 1998; the entire contents of these applications are hereby incorporated by reference. This application is also related to U.S. patent appl Ser. No. 08/712,967, filed Sep. 12, 1996, now U.S. Pat. No. 5,788,957; U.S. patent appl Ser. No. 08/211,749, having priority date Oct. 15, 1992, now U.S. Pat. No. 5,626,865; and U.S. patent appl Ser. No. 07/776,211, filed Oct. 15, 1991, now U.S. Pat. No. 5,270,051; the entire contents of each are hereby incorporated by reference.

FIELD OF THE INVENTION

The present invention relates to methods for accelerating non-surgical corneal reshaping involving the release of corneal hardening agents which facilitate reshaping of the cornea to correct refractive errors of the eye.

BACKGROUND OF THE INVENTION

The cornea is the clear dome on the front of the eye. About eighty percent of the focus, or refracting, power of the eye is at the cornea. When the cornea is misshapen or the axial length of the eye is too long or too short, or when the lens of the eye is functioning abnormally, the refractive errors of myopias (nearsightedness), astigmatism (blurred vision) or hyperopia (farsightedness) can result. Throughout history, mankind has experimented with ways to improve vision. Although these ways have provided many people with a reasonable quality of life, they still have limitations.

Glasses correct refractive errors of the eye by changing the angle at which the light enters the cornea by refracting the light with a lens before it reaches the cornea. But for many lifestyles, glasses are very inconvenient. And for some people, they do not give the quality of vision desired. When the glasses are taken off, the refractive error still exists. Contact lenses correct refractive errors of the eye by replacing the defective corneal curve with the front curve of a contact lens that is calculated to render the eye emmetropic, which is a state where no visual correction is necessary. But wearing contact lens also has a price. The wearer must spend considerable time and money both in the maintenance and the application of the contacts. There still remains a limitation as to the types of activities in which one can participate. And, lastly, long term lens wearers may develop an intolerance to wearing their lenses as well as long term damage. When the lens is removed, the refractive error still remains.

Radial Keratotomy ("RK") is a surgical operation to improve myopia by changing the curve of the cornea over the pupil. The surgeon makes several deep incisions in the cornea in a radial or spoke-like pattern. The incisions are intended to flatten out the central cornea to correct the patient's vision. However, RK can only be used to correct low amounts of myopia. It cannot address the problems of hyperopia. The main drawback is that the cornea is seriously weakened and frequently continues to change shape with time. A newer type of RK that involves making shorter incisions is replacing standard RK. But newer techniques using computerized assessment, precisely calculated cutting patterns, and lasers will probably result in the rapid decline of RK.

Photorefractive Keratectomy ("PRK") is a surgical procedure similar to RK involving the use of an excimer laser, which is controlled by a computer that measures the shape of the eye and sets the power of the laser. With the PRK process, the excimer laser permits the ability to sculpt rather than cut the surface of the cornea. There are a combination of laser machines that with a combination of computer controls can reliably treat myopia, hyperopia, and astigmatism. However, since PRK is a surgical procedure, it can result in complications. Infection is the most serious complication. Other possible problems include delayed surface healing, corneal haze or scarring, over or undercorrection, and the development of astigmatism. Some individuals can have a poor or excessive healing response. The complications must be treated with medications or further surgery.

Laser in-situ keratomileusis ("LASIK") is a surgical procedure that is a variation on PRK involving an excimer laser and a precise cutting machine called a microkeratome. An ophthalmologist uses the microkeratome to form a circular flap on the cornea. The flap is flipped back, as if on a hinge, to expose the inner layers of the cornea. With the flap folded back, the doctor now makes the refractive correction on the inner layers of the cornea using the excimer laser. Finally, the flap is repositioned to complete the procedure. With a precision laser treatment and normal reattachment and healing of the flap, the refractive results can be rapid and superb. There is, however, a very significant list of potential complications and risks including failure of the microkeratome to leave a hinge on the corneal flap with the first incision, loss of the corneal flap during the operation, loss of the corneal flap after the operation, slipping of the flap and healing off center, first incision too deep or too shallow, invasion of the surface tissue into the central tissue of the cornea, infection of the cornea, loss of visual acuity from scarring or optical distortion due to the flap not being repositioned correctly, technical problems with complex and finicky automated cutting devices, and the procedure being much more dependent upon the surgeon's operating skills than the computerized precision of the procedure.

Thermokeratoplasty is another corneal reshaping method. In thermokeratoplasty heat is applied to the cornea to induce shrinkage. Corneal stromal collagen shrinks when heated to a temperature of 55° C. to 58° C., without the destruction of the tissue. If the pattern of shrinkage is properly selected the resulting change in the stress field and mechanical properties caused by the shrunken collagen fibers can be used to reshape the cornea.

A variety of methods are known with which to practice thermokeratoplasty. For example, U.S. Pat. No. 4,881,543 discloses one method and apparatus for heating the central stroma of the cornea with microwave electromagnetic energy to the shrinking temperature of the collagen while circulating a cool fluid over the anterior surface of the cornea. In another example, U.S. Pat. No. 5,779,696 describes the use of light energy to reshape the cornea in a process known as photothermokeratoplasty. All of the processes suffer from a variety of shortcomings, including a common flaw in which corneas in the treated subjects are unstable after the thermokeratoplasty procedure is concluded.

Orthokeratology is a non-surgical procedure designed to correct refractive errors by reshaping the cornea to the curvature required for emmetropia. This is accomplished by applying a series of progressive contact lens changes that retrain the eye to achieve a corneal curvature. However, once a desired corneal curvature has been produced, retainer contact lenses must be worn to stabilize the results or regression may occur.

Enzyme Orthokeratology is related to traditional Orthokeratology in that it is defined primarily as a contact lens procedure of correcting refractive errors by reshaping the cornea to the curvature required for emmetropia. The program is supplemented by chemically softening the cornea. By supplying drugs that soften the cornea, the cornea is chemically reshaped by being molded to the concave surface of a contact lens having a predetermined curvature. The contact lens radius is selected to render the eye emmetropic. Retainer contact lenses will not be required for good visual acuity after removal of the contact lens from the cornea and regression will not be a problem. However, the length of program of treatment varies from weeks to months with progressive contact lens changes and periodic follow-up examinations.

Notwithstanding the foregoing, there remains a need for non-surgical methods of correcting refractive errors of the eye which can correct various degrees of refractive error and produce relatively permanent results in a much shorter period of time.

SUMMARY OF THE INVENTION

An Enzyme Orthokeratology method is provided for correcting refractive errors in the eye of a subject mammal. Accelerating reshaping of the cornea is accomplished by administering a corneal hardening amount of a corneal hardening agent to the eye of the subject. Reformation is accomplished under the influence of a rigid contact lens or a series of lenses having a concave curvature that will correct a refractive error. The cornea rapidly reshapes its convex curvature to the concave curvature of the contact lens, rendering the eye emmetropic. The cornea is permitted to "harden" to retain the new emmetropic shape. After "hardening" has occurred, the lens rendering the eye emmetropic is removed.

A method for correcting refractive errors in an eye of a subject mammal, comprising the steps of selecting a pharmaceutically acceptable corneal hardening agent on the basis of its being able to harden the cornea in the eye of the subject without causing damage to the cornea, administering to the eye of the subject a corneal hardening amount of the agent so that the cornea can be reshaped from a first configuration to a desired second configuration, fitting the cornea with a rigid contact lens having a concave curvature of the desired second configuration, permitting the cornea to reshape to the desired second configuration under the influence of the lens, and removing the lens when the cornea is capable of maintaining the desired second configuration without the support of the lens.

Preferably, the types of refractive errors are selected from the group consisting of myopia, hyperopia and astigmatism and the corneal hardening agent is a cross linker such as an aldehyde. This aldehyde may be selected from the group consisting of acetaldehyde, glyceraldehyde, phenylacetaldehyde, valeraldehyde, 3,4-dihydroxyphenylacetaldehyde, mutarotational isomers of aldehydes, ascorbic acid and dehydroascorbic acid. The corneal hardening agent may also be an enzyme, where the enzyme mediates cross linking reactions. Examples of a suitable enzyme include lysyl oxidase or prolyl oxidase. In one embodiment, the corneal hardening agents may be administered by injection into the eye, by topical administration into the eye in the form of eye drops or by means of a contact lens.

In another embodiment, the additional step of administering to the eye a corneal softening amount of a pharmaceutically acceptable corneal softening agent sufficient to soften the cornea of the eye so that the cornea can be reshaped is performed as part of the method to correct a refractive error. In this embodiment, the corneal softening agent is an enzyme that degrades proteoglycans in the cornea, such as hyaluronidase.

Another embodiment of the present invention is a kit for performing refractive corrections in an eye of a subject mammal, comprising: a corneal hardening agent in unit dosage form and a rigid corrective lens having a desired concave structure.

Still another embodiment of the present invention is a reaction mixture comprising: the eye of a subject mammal, a corneal hardening agent in unit dosage form; and a rigid corrective lens having a desired concave structure.

Yet another embodiment is a method of rehabilitating corneal irregularity and correcting refractive error in an eye of a subject mammal with irregular corneal shape, comprising the steps of: identifying a subject with irregular corneal shape, selecting a pharmaceutically acceptable corneal hardening agent on the basis of its being able to harden the cornea in the eye of the subject without causing damage to the cornea, administering to the eye of the subject a corneal hardening amount of the agent so that the cornea can be reshaped from a first configuration to a desired second configuration, fitting the cornea with a rigid contact lens having a concave curvature of the desired second configuration, permitting the cornea to reshape to the desired second configuration under the influence of the lens, and removing the lens when the cornea is capable of maintaining the desired second configuration without the support of the lens. Subjects may be identified for this procedure by diagnosing them as having a condition selected from the group consisting of: keratoconus, contact lens induced corneal warpage, contact lens intolerance, corneal ulcers, corneal melting disorders, recurrent corneal erosions, pterygium, and irregular corneal shape or uncorrected refractive error due to corneal surgery.

Another embodiment of the present invention is a method for improving the clinical success of surgery to the eye involving the manipulation of a cornea of a subject mammal, comprising the steps of: identifying a subject who has undergone a corneal manipulation, selecting a pharmaceutically acceptable corneal hardening agent on the basis of its being able to harden the cornea in the eye of the subject without causing damage to the cornea, administering to the eye of the subject a corneal hardening amount of the agent so that the cornea can be reshaped from a first configuration to a desired second configuration, fitting the cornea with a rigid contact lens having a concave curvature of the desired second configuration, permitting the cornea to reshape to the desired second configuration under the influence of the lens, and removing the lens when the cornea is capable of maintaining the desired second configuration without the support of the lens. In this embodiment, the typical corneal manipulations are selected from the group consisting of radial keratotomy, photorefractive keratectomy, LASIK, thermokeratoplasty, corneal transplant surgery, cataract surgery, and corneal reshaping by laser.

BRIEF DESCRIPTION OF THE DRAWINGS

FIG. 2 is Table II, showing result for use of 50 IU hyaluronidase injection, corrective lenses and 3% glyceraldehyde solution.

FIG. 3 is Table IIIA, showning results for use of 500 IU hyaluronidase injection, corrective lenses and 3% glyceraldehyde solution.

FIG. 4 is Table IIIB showing results for use of 500 IU hyaluronidase injection, corrective lenses and 3% glyceraldehyde.

FIG. 5 is Table IV, showing results for use of corrective lenses and 3% glyceraldehyde solution.

DETAILED DESCRIPTION OF THE PREFERRED EMBODIMENT

Figure 1:
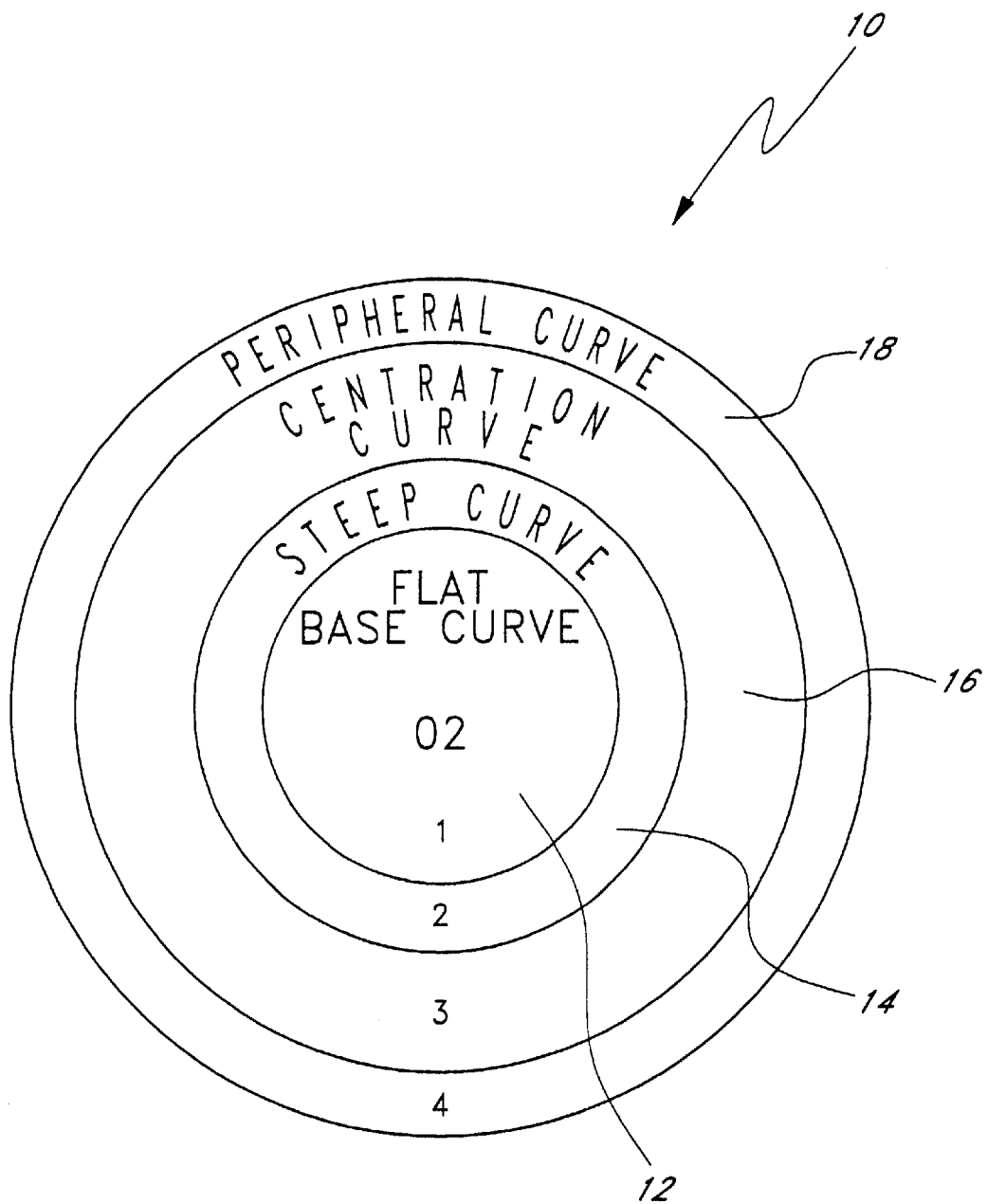
FIG. 1 shows a plan view of an Enzyme Orthokeratology rigid gas permeable lens for use in treating myopia.

Enzyme Orthokeratology includes the use of one or more enzymes and/or the use of other agents in conjunction with a Orthokeratology contact lens program. In a traditional Orthokeratology program, a misshapen cornea is treated with a corrective lens to alter its shape and eliminate a vision impairment. This procedure bends or compresses the misshapen cornea from a defective first position to a more optimum second position. This procedure produces a reshaped cornea in which the visual defect has been eliminated. Unfortunately, these effects are not permanent. Since the underlying structural components of the cornea are unchanged, the corneal shape now in an optimized second position will eventually revert to the defective first position in the absence of the corrective lenses.

In contrast to traditional Orthokeratology, the methods of Enzyme Orthokeratology according to the invention alter the shape of the cornea using a corrective lens and preserve the desired second position induced by the corrective lenses. This preservation is achieved by altering and hardening the structural components of the cornea. Corneal hardening may be achieved by inducing cross links between the components of the cornea. Cross links are chemical bonds formed between corneal components. These cross links preserve a structural change induced in the cornea as a result of wearing corrective lenses. In this way, corneas treated with Enzyme Orthokeratology according to the invention may take on and hold a new shape that eliminates a vision impairment, preferably without any need for the continued use or support of contact lenses.

In the methods of Enzyme Orthokeratology provided herein, enzymes and/or other agents alter and modify the structural corneal components. These enzymes or agents may be administered to harden the cornea into the desired second configuration induced by a corneal shape correcting methods such as Orthokeratology. The term "harden" is used herein to denote the modification or cross linking of corneal components. This hardening results in an increased ability of a treated cornea to preserve the desired second configuration after the active treatment regime has concluded.

I. Structure and Components of the Cornea

The cornea itself is composed of five layers. The outermost layer is the epithelium, which is 4–5 cells thick. Beneath the epithelium is the acellular Bowmans membrane. The middle layer is the stroma, which is composed of scattered corneal fibroblasts (keratocytes) among organized lamellae of collagen, proteoglycans and glycoproteins. Below the stroma is another acellular layer called Descemet's membrane. The innermost layer of the cornea, comprised of a single layer of flattened cells, is the endothelium.

The stroma makes up the bulk of the cornea. It composed of highly organized collagen, which accounts for the transparency of the structure. The acellular components of the stroma consist mainly of collagen, proteoglycans and glycoproteins. The collagen is organized into lamellae that are in turn made up of flattened, parallel bundles of collagen fibrils. The keratocytes secrete the stromal lamellae. Of the various types of collagen in existence, collagen of more than one type has been identified throughout the stroma.

The corneal stroma is composed of 78% water, 1% salts, and 21% biological macromolecules, almost 75% of which is collagen fibrils. Collagen is a family of fibrous proteins of novel structure and function. It is the most abundant protein in mammals and serves, in part, to hold cells together. There are a number of types of collagen, classified by their amino acid structures. Structurally, a collagen fibril is composed of three protein chains coiled about each other in a triple helical conformation.

Collagen has a very unusual amino acid sequence. Nearly every third amino acid residue is a glycine. In contrast, hemoglobin has a glycine content of only five (5) percent. Furthermore, collagen has an unusually high concentration of the proline and lysine derivatives 4-hydroxyproline and 5-hydroxylysine. These amino acid derivatives play a crucial role in determining the structure of the collagen fibril since they are frequently modified and often form cross links.

Lysine amino acids may be modified to alter the structure of the corneas. These residues may be cross linked through an aldol condensation. These cross links serve to strengthen the collagen fibers, presumably by reinforcing the collagen triple helix. The importance of these cross links is apparent when one considers the disease scurvy. Scurvy is caused by a deficiency of ascorbic acid. Ascorbic acid is a cofactor in the formation of hydroxypyridinium cross links between two hydroxylysine residues and one lysine residue. The degradation of connective tissue that is a hallmark of scurvy is due, in part, to a lack of collagen cross links.

The modification of collagen proline residues may also effect the structure of the protein. The extent of proline hydroxylation has been shown to effect the thermal stability of collagen. Collagens from a variety of sources exhibiting varying degrees of hydroxylation were examined to determine their respective temperatures of melting. Interestingly, collagen containing a higher percentage of hydroxyproline melted at a higher temperature than collagen with lower percentages of hydroxylation.

The connective tissue of the cornea is also rich in proteoglycans. Proteoglycans are composed of a hyaluronate core, a protein core, and glycosaminoglycans, which are proteoglycan monomers with repeating disaccharide units. Approximately 60% of the glycosaminoglycans of the cornea are made up of keratan sulfate, while the remaining 40% are mostly chondroitin sulfate.

II. Hardening Agent Used in Enzyme Orthokeratology

A number of enzymes and agents may be used to perform the corneal hardening function of Enzyme Orthokeratology according to the invention. Of particular interest are cross linking agents and corneal hardening enzymes. However, Enzyme Orthokeratology according to the invention is not limited to the use of these enzymes and agents, and includes chemicals that can be administered to harden a cornea through various different mechanisms of action.

Federal law requires that the use of pharmaceuticals in the treatment of patients be approved by an agency of the Federal government, the Food and Drug Administration. Similar approval is required by most foreign countries. Only pharmaceutical-grade forms of enzymes and agents are to be used in the practice of the present invention in accordance with the laws of the forum state.

Corneal hardening agents are to be selected on the basis of safety and efficacy. As in conventional Enzyme Orthokeratology, the present invention is related to traditional Orthokeratology in that it is defined primarily as a contact lens procedure of correcting refractive errors by reshaping the cornea to the curvature required for emmetropia. However, the program is supplemented by chemically hardening the cornea. By supplying drugs that harden the cornea, the cornea is chemically reshaped by being molded to the concave surface of a contact lens having a predetermined curvature. The contact lens radius is selected to render the eye emmetropic. Retainer contact lenses will not be required for good visual acuity after removal of the contact lens from the cornea and regression will not be a problem. The complications and risks of surgery will be prevented by virtue of following these non-surgical steps.

A. Aldehydes Used In Enzyme Orthokeratology

An aldehyde is a carbonyl group bonded to one carbon atom and one hydrogen atom. Formaldehyde, the simplest example of an aldehyde, is an exception to this rule since it has two hydrogen atoms bonded to the carbonyl group. A carbonyl group is a carbon-oxygen double bond with the carbon having two available sites to bond with other atoms. The chemical nature of the carbonyl group, namely the double bond and the ability of oxygen to orbit six free electrons, taking two from the double bond, makes this group extremely reactive.

One chemical reaction in which aldehydes frequently engage is called the aldol condensation reaction. In one aspect of the present invention, aldehydes are reacted with each other to form cross links within corneal components using the aldol condensation reaction. In a typical aldol condensation reaction, the carbonyl group undergoes an enolization where an enolate anion is formed. An enolate anion is formed when one pair of electrons is shifted to the carbon of the carbonyl group from a neighboring carbon atom. A proton acceptor may remove a proton from the neighboring carbon atom in the reaction, and if that acceptor is a hydroxyl then water is formed. As the electrons shift to the carbon of the carbonyl group a double bond is formed between it and the neighboring carbon atom. This shift in electrons causes a pair of electrons to shift from the carbonyl carbon to the carbonyl oxygen, creating a negative charge on that oxygen. The resulting carbon-carbon double bond of the enolate reaction is extremely reactive.

The electrons from the enolate anion's carbon-carbon double bond attack the carbonyl group of a neighboring aldehyde molecule resulting in a joining or condensation of the two molecules The resulting compound is an alkoxide that may then be protonated to yield a hydroxyaldehyde. The aldol condensation reaction can be used by the present invention to cross link various corneal structural molecules, including lysine residues located in corneal collagen proteins in a neutral pH without the addition of an additional catalyst, strong acid or base.

Corneal collagen contains an unusually large number of lysine residues. The amine groups at the ends of the lysines side chains are used to cross link lysine-containing collagen proteins. In the positively charged ammonium state, lysyl oxidase oxidizes the carbon to which the ammonium group is attached. The nitrogen group leaves resulting in the creation of an aldehyde derivative of lysine called allysine. The aldehyde groups of neighboring allysines may engage in an aldol condensation. The reaction of the two side chains results in a cross link between the two amino acids.

Lysyl oxidase also plays a role in the formation of a three way lysine product known as a hydroxypyridinium cross link. Four residues in each tropocollagen molecule may participate in this type of cross link. These include a lysine residue near the amino terminus, a lysine near the carboxyl terminus, and hydroxylysines in the helical region near the ends of the collagen molecule. Typically hydroxypyridinium cross links are formed between residues of the amino terminus of one collagen molecule and the carboxyl terminus of a neighboring molecule. In a proposed reaction pathway, hydroxylysine is first converted to hydroxyallysine by lysyl oxidase. A mechanism of formation has been proposed where two divalent ketoamine cross links may interact to produce one trivalent 3-hydroxypyridinium cross link. The formation of hydroxypyridinium cross links may be an important mechanism in the functioning of the present invention.

The present invention contemplates the use of a variety of different aldehydes to cross link constituent corneal structures particularly collagens and proteoglycans. Those aldehydes include acetaldehyde, glyceraldehyde, phenylacetaldehyde, valeraldehyde, 3,4-dihydroxyphenylacetaldehyde, glycoaldehyde (the aldehyde form of ethylene glycol), pyruvaldehyde, dihydroxy acetone, acetol, glyoxal, and mutarotational isomers of aldehydes including glucose, fructose, lactose, and other sugars.

Other contemplated cross linking agents include additional aldehyde compounds and ascorbic acid and dehydroascorbic acid.

Aldehydes that contain α-hydrogen can be useful cross linking agents in that they can react with N-acetyl groups of glycosaminoglycan chains in corneal proteoglycans to produce long chain polymeric proteoglycans.

In one embodiment of the present invention, the primary aldehyde used to harden a cornea is glyceraldehyde. Commonly used scientific names for this aldehyde include: glyceraldehyde, 2,3-dihydroxypropional and α,β-dihydroyxypropionaldehyde. Glyceraldehyde is the simplest aldose and a derivative of this molecule, glyceraldehyde 3-phosphate, is a metabolic intermediate product of carbohydrate metabolism. The fact that a derivative of glyceraldehyde plays such an important role in cellular metabolism implicates the safety of this compound when used to reshape the cornea in an otherwise healthy eye.

Glyceraldehyde may be obtained from a variety of sources including Sigma Chemical Company, Inc., St. Louis, Mo.; Aldrich Chemical Company, Inc., Milwaukee, Wis.; Fluka Chemical Corp., Ronkonkoma, N.Y.; Fisher Scientific, Pittsburgh, Pa. Glyceraldehyde exists as a tasteless solid with a melting point of 145° C. It is a monosaccharide with the empirical formula $(CH_2O)_3$ and a molecular weight of 90.08. Presently purity may vary among commercial suppliers of glyceraldehyde, ranging from approximately 95% to 98%. The invention should only be practiced with the purist form of this compound.

In furthering the present invention, the glyceraldehyde ophthalmic solution was prepared under sterile conditions by dissolving glyceraldehyde into a volume of 0.9% sodium chloride solution, USP, (McGaw Pharmaceuticals, Invine, Calif.) followed by subsequent sterile filtration. Other drugs such as proparacaine or tropicamide may be included to anesthetize the cornea.

The optimum concentration of glyceraldehyde may vary depending on the protocol, the nature of the delivery vehicle, and the number of administrations. In general, concentrations of glyceraldehyde will vary within the range of about 0.01% to 10% weight to volume (w/v). In one embodiment, the concentration range of the glyceraldehyde solution will vary from 1% to 5% (w/v). In still another embodiment, the concentration of 3% glyceraldehyde is used.

It is further noted that aldehydes other than glyceraldehyde are contemplated for use in the present invention. Such compounds include acetaldehyde, glyceraldehyde, phenylacetaldehyde, valeraldehyde, 3,4-dihydroxyphenylacetaldehyde, glycoaldehyde (the aldehyde form of ethylene glycol), pyruvaldehyde, dihydroxy acetone, acetol, glyoxal, and mutarotational isomers of aldehydes including glucose, fructose, lactose, etc. Suitable alternative aldehydes have biochemical characteristics similar to those of glyceraldehyde possessing α-hydrogen, including biodegradability, low toxicity, and ready readsorption into the treated area.

B. Enzymes Used In Enzyme Orthokeratology

In one aspect of the present invention, enzymes are used as corneal hardening agents. These enzymes increase corneal rigidity by modification of corneal structural components. These structural modifications comprise of covalent intra- and/or intermolecular cross links, hydroxylation, or other modifications. In one example, the formation of collagen cross links may be exploited to increase corneal rigidity or hardness using the methods of the present invention.

In one embodiment, lysyl oxidase is used as an enzymatic corneal hardening agent. The enzyme lysyl oxidase plays a central role in the formation of collagen cross link formation. Lysyl oxidase is a 30-kd metalloenzyme which converts the amine side chains of specific lysine and hydroxylysine residues in collagen into aldehydes. Once the enzyme has converted the collagen lysine residues to their aldehyde derivatives, neighboring lysine residues may form cross links by undergoing the aldol condensation reaction described above. The formation of collagen cross links serve to reduce the mobility of individual collagen molecules within the matrix of the cornea, thus increasing the rigidity of the structure.

In another embodiment enzymes which hydroxylate collagen residues may be used as corneal hardening agents. It is known in the art that certain lysine and proline residues are hydroxylated by lysyl hyroxylase and prolyl hydroxylase respectively in vivo. These modifications may also be exploited to induce corneal rigidity or hardness.

For example, the extent of proline hydroxylation has been shown to effect the thermal stability of collagen. Thermal stability of a protein reflects the structural stability of the molecule and may denote the presence of stabilizing components within the protein. Collagen from a variety of sources exhibiting varying degrees of hydroxylation was examined to determine their respective temperatures of melting. Interestingly, collagen containing a higher percentage of hydroxyproline melted at a higher temperature than collagen with lower percentages of hydroxylation. This correlation between the respective temperatures of melting and the extent of proline hydroxylation implies that an increase in this modification may stabilize the collagen protein. Accordingly, hydroxylases may also be used to induce corneal hardness.

In another embodiment, hydroxylation may be used as a preliminary enzymatic step preparing corneal collagen for glycosylation. Here, lysine or proline residues in collagen would be hydroxylated with lysyl hydroxylase or prolyl hydroxylase respectively. These residues could then be glycosylated through the action of an enzyme like galactosyl transferase and/or glucosyl transferase. These modifications would also result in the induction of corneal hardness and are therefore suitable for use in the present invention.

In addition to these enzymes, other enzymes known in the art that alter and modify protein structure may be used with the methods of the present invention. Suitable enzymes induce protein modifications that increase corneal rigidity.

C. Oxidative Hardening Agents Used in Enzyme Orthokeratology

An additional group of reagents that are known in the art to induce protein crosslinking are the oxidative crosslinking agents. These reagents act by producing oxygen free radicals. In turn, oxygen free radicals interact with labile sites in the cornea resulting in the induction of inter- and intramolecular chemical bonds.

One group of these reagents includes various sulfate compounds that are used to form cross-links. Examples of these compounds include copper sulfate ($CuSO_4$) and iron sulfate ($FeSO_4$). Ascorbic acid and $CuSO_4$ or $Fe_2(SO_4)_3$ and other complexes of copper and iron act as oxidative crosslinking agents. Examples of these complexes include cuproxoline, caeluroplasmin, transferrin, lactoferrin, cupric gluconate, and others.

Chromium sulfate $Cr_2(SO_4)_3$ is another compound that is usable as an oxidative cross-linking agent.

The use of ultraviolet light (UV) is also contemplated to induce oxidative cross-links. The judicious use of UV alone or in combination with various photosensitizers is contemplated for use to induce oxidative cross-links. Examples of photosensitizers include riboflavin, psoralen, Rose Bengal, methylene blue, and others.

These oxidative cross-linking methods can be used alone to induce cross-links in a subject, or may be using in combination with the aldehyde or enzymatic cross-linking methods when compatible. For example, UV and ascorbic acid may be used in conjunction to induce cross-linking. Conversely, $CuSO_4$ and lysyl oxidase may not be used simultaneously since, as is well known in the art, $CUSO_4$ inhibits lysyl oxidase activity.

D. Determining Corneal Hardening Agents and Their Dosages

The corneal hardening chemicals, such as various agents and enzymes, used in the methods of the present invention, in addition to the proper dosages of such agents and enzymes, can be determined by one of skill in the art through routine experimentation. Such experimentation can comprise testing a dose of an enzyme or agent on donor globes (eyes) mounted in plastic model sockets or testing such a dose on laboratory animals. Briefly, to determine an appropriate corneal hardening amount of a known hardening agent or enzyme, or an agent or enzyme to be tested for its ability to produce corneal hardening, a dose of the agent or enzyme is administered to a cornea in a donated eye or a cornea of a test animal, and the hardening and toxic effect of the agent is thereafter determined.

In order to determine whether an enzyme or agent is effective in hardening a cornea without producing toxicity, or, if it is a known hardening agent, whether a particular dosage will produce corneal hardening without causing toxicity, the enzyme or agent is first mixed in a carrier vehicle that is pharmaceutically acceptable to a mammal. Preferably, the enzyme or agent is in lyophilized (dry powder) form, and is dissolved in isotonic saline. However, one of ordinary skill in the art will understand that a variety of pharmacologically acceptable carriers which do not interfere with the functioning of an enzyme or agent can be used.

A test dose of the enzyme or agent in solution is then administered to a test cornea in order to determine its corneal hardening and toxic effect. In one procedure for testing candidates, the test enzyme or agent is first administered to donor globes (eyes from a human donor) mounted in plastic sockets. This procedure is particularly preferred for determining the effect of an enzyme or agent on a human cornea because in this way a human cornea can be tested without subjecting a living person to experimentation. A donor globe used in this procedure is prepared for experimentation by injecting it with sufficient saline to maintain intraocular pressure of the globe at approximately 20 mm Hg.

The test dose of enzyme or agent is then administered to the donor cornea. Such administration can be, for example, by injection of the enzyme into the cornea. Normally, the lens will become opacified following this step due to the introduction of water into the eye and a change in the refractive index of the eye. After a test period of time, the mounted globe is then examined to determine whether any corneal hardening or toxicity has occurred, and if so the extent of such hardening and toxicity.

The examination of the cornea can be performed, for example, through slit-lamp examination to determine the clarity of the cornea; pachymnetry to measure the thickness of the cornea; computer-assisted corneal topography to evaluate surface topographical changes; measurement of the tensile strength of the cornea; measurement of the distensibility of the cornea; keratometry to measure central corneal curvature; and retinoscopy to measure the refractive error of the cornea. The values determined from these tests are compared to values determined prior to the administration of the agent or enzyme.

In addition, a treated cornea in a mounted globe can be subjected to a number of other tests to determine the strength and viability of the cornea following treatment. For example, light, scanning, x-ray diffraction analysis, and transmission electron microscopy can be used to examine the morphology of the cornea; tissue culture is prepared to determine the viability of the cells of the cornea following treatment; biochemical studies can be made of the collagens and other structural components of the cornea following treatment.

The foregoing tests of donated globes and corneas can be used to verify that use of a particular enzyme or agent does not compromise the transparency of the cornea, decrease the viability of the corneal cells, or damage the structural integrity of the cornea. Testing the use of an enzyme or agent on the cornea of a test animal, however, is also desirable in order to make sure that the candidate has no unexpected effect in living mammals that is not discovered during tests of donated eyes. In order to test the effect of a particular test enzyme or agent, a test dose in a pharmacologically acceptable carrier solution is administered to a test animal, in this case a mammal, so as to deliver that agent to the cornea of the animal.

Following the administration of an agent to the cornea of the animal, the animal's cornea can be subjected to the following examinations: slit lap examination to determine the clarity of the cornea, anterior chamber and iris; pachymetry to measure corneal thickness; computer assisted corneal topography to evaluate the surface topographical change of the cornea; measurement of the elasticity of the cornea; tonometry to measure intraocular pressure; flndoscopic examination in order to evaluate the optic nerve and retina; keratometry to measure central corneal curvature; retinoscopy to measure refractive error; staining with fluorescein or Rose Bengal to identify damage to the corneal epithelium; and indirect ophthalmoscopy. The values determined through these tests can be compared to values determined prior to the administration of the enzyme or agent, as well as to values determined for the untreated eye of the animal.

In addition, a treated cornea of a test animal can be subjected to a number of other tests to determine the strength and viability of the cornea following treatment. For example, light, scanning, and transmission electron microscopy can be used to examine the morphology of the cornea; a tissue culture is prepared to determine the viability of the cells of the cornea following treatment; and biochemical studies can be made of the collagens and other structural components of the cornea following treatment.

Other corneal hardening enzymes and agents not disclosed herein and proper doses of such known and unknown enzymes and agents can be determined as described hereinabove in relation to determining enzymes and doses of enzymes.

In another embodiment of the invention, a corneal softening agent is first administered to a plurality of donor globes or to the corneas of an experimental animal, as described above. Corneal softening agents include various enzymes and agents, for example, proteases and proteoglycan degrading enzymes, advantageously, hyaluronidases. When using experimental animals, once the corneas have begun to soften, one cornea of the experimental animal is then treated with a test dose of the enzyme or agent to be tested for its hardening and toxic effect in order to determine whether the dose of the enzyme or agent can harden or toxify the cornea. The other cornea is left alone as a control. When using donor globes, a plurality of corneas can be tested, as long as one is left untreated as a control. The treated corneas can then be tested with a dose of test enzyme or agent. The control cornea and tested corneas should be treated for approximately the same amount of time in order to be able to make a valid comparison of the effectiveness of the test enzymes and agents on the tested corneas.

After a period of time, the hardness or extent of hardening in a previously softened cornea as well as toxicity is compared using the procedures described above with reference to determining the extent of corneal hardness and toxicity induced by an experimental enzyme or agent. If the treated cornea is harder than the control, the test dose of the candidate may be determined as being useful in inducing corneal hardening, and if the treated cornea is the same as the control then the test does of the candidate may be concluded to be safe as not causing damage to the cornea. An optimal dose may also be established using this method.

The present invention further provides a kit for the preparation and use of the corneal hardening and softening agents from individual components. The kit will comprise a first container holding a hardening agent and a second container holding a softening agent. In addition, the kit will include instructions to prepare the agents for use by individually combining them with a pharmaceutically acceptable carrier.

III. Methods of Administering Corneal Hardening Agents

The foregoing enzymes and agents for hardening a cornea may be administered in any way known to the art. For example, in one embodiment, an enzyme or agent is injected directly into the eye in a location proximal to the cornea. In this embodiment, the enzyme or agent should be mixed in a pharmacologically acceptable carrier which will not alter the effectiveness of the enzyme or agent contained therein.

In another embodiment of the present invention, corneal hardening enzymes and agents are administered to the eye of a subject by topical application in the form of eye drops. A sufficient number of drops are applied so as to administer a desired concentration of enzyme or agent to the cornea of the subject. The eye drop method of administration may be superior to injection based administration based on the less discomfort to the cornea of the subject resulting from an injection technique.

In still another embodiment, alternative means of aiding diffusion across the eye into the cornea may be used. Such means include, for example, the use of liposomes to deliver the active enzyme or agent. The enzyme or agent is packaged into liposomes, which can pass across the lipid soluble membrane of the corneal epithelium and into the corneal stroma. Other means of aiding difflusion include the use of an electrical current to make the outer membrane of the eye more permeable to the passage of enzymes and agents, known as iontophoresis. Using this procedure, an electrical current traveling through a salt solution causes the agents to pass into the eye as charged particles.

Compounds that enhance the ability of the active compounds of the present invention to penetrate the cornea are contemplated. A variety of compositions are envisioned for use as vehicles by which to administer the active agents of the present invention to the eye of a subject mammal. A list of substances includes: acidifying agent, aerosol propellant, air displacement, alcohol denaturant, alkalizing agent, anticaking agent, antifoaming agent, antimicrobial preservative, antioxidant, buffering agent, capsule lubricant, chelating agent, coating agent, color, complexing agent, desiccant, emulsifying and/or solubilizing agent, filtering aid, flavors and perfumes, glidant and/or anticaking agent, humectant, ointment base, plasticizer, polymer membrane, solvent, sorbent, carbon dioxide, stiffening agent, suppository base, suspending and/or viscosity-increasing agent, sweetening agent, tablet binder, tablet and/or capsule diluent, tablet disintegrant, tablet and/or capsule lubricant, tonicity agent, vehicle, viscosity increasing, water repelling agent, wetting and/or solubilizing agent. In one embodiment using glycerol aldehyde, the divalent cation chelator ethylenediaminetetracetic acid (EDTA) and phosphate buffered saline solution at a pH of 8.0–8.5 was effective.

In alternative embodiments, sustained release vehicles are used. Sustained release vehicles are compositions that act to hold the active ingredients of the present invention in functional association with the cornea. Compounds and compositions in the sustained release technology are well known in the art. (See, Controlled Drug Delivery, $2^{nd}$ ed., Joseph R. Robinson & Vincent H. L. Lee, Eds., Marcel Dekker, Inc., New York, 1987). By holding the active ingredients in association with the cornea to be treated, a sustained release vehicle acts to increase the efficacy of the active ingredients of the present invention. This increase in efficacy can be attributed to the sustained release vehicle acting to raise the local concentration of the active ingredients of the present invention with respect to the treated cornea to levels higher than would be possible without the sustained release vehicle.

Sustained release vehicles for use with the present invention hold or localize the active agents of the present invention in proximity to the cornea and have no detrimental effects on the cornea or the activity of the agents of the present invention. In a preferred embodiment, the sustained release vehicle is water soluble. Examples of suitable sustained release vehicles include: cellulose ethers such as methyl cellulose, methyihydroxypropyl cellulose, methylhydroxyethyl cellulose, hydroxypropyl cellulose, hydroxyethyl cellulose, and sodium carboxymethyl cellulose. Cellulose esters such as cellulose acetate phthalate and hydroxypropyl methyl cellulose phthalate; polymers derived from at least one acrylic acid, acrylic acid esters, methacrylic acid and methyacrylic acid esters such as methacrylic acid-methyl methacrylate polymer and theacrylic acid-ethylacrylate copolymers are also contemplated for use with the present invention. Additional polymers contemplated for use with the present invention include polymers derived from methylvinyl ether and maleic acid anhydride, polyvinylpyrrolidone, polyvinyl alcohols, and the like, as well as mixtures of any of the compounds named above.

Those of ordinary skill in the art would know at what concentrations to use these compounds. In one embodiment, polymer concentrations range from about 0.001% to about 5.0%. In another embodiment, the concentrations range from about 0.1 to about 1.0%. An example of sustained release formulation containing the corneal hardening agent glyceraldehyde would comprise glyceraldehyde at 3%, sodium carboxymethyl cellulose at 0.5% and bring the total volume to 100 milliliters.

In yet another embodiment of the present invention, corneal hardening enzymes and agents are administered to the cornea through use of a contact lens. As will be discussed in more detail below, the methods of the present invention involve the application of a rigid contact lens to a cornea in a suboptimal first conformation in order to reshape that cornea to a desired second conformation. In one embodiment of the present invention, the fitting of the contact lens and the administration of a corneal hardening enzyme or agent occurs simultaneously. In an alternative embodiment of the present invention, the fitting of the contact lens and the administration of a corneal hardening enzyme or agent occurs sequentially.

As an example of one embodiment of the present invention, a corneal hardening amount of a corneal hardening agent is loaded into a chamber inside a rigid contact lens, preferably one which is gas permeable. Alternatively, the enzyme or agent can be loaded or impregnated into a soft lens capable of taking up the enzyme or agent by soaking the soft lens in a solution containing the enzyme or agent. The enzyme or agent can also be loaded into a combination of a soft and a rigid lens.

In all of the following embodiments of a contact lens for administering a corneal hardening enzyme or agent, the enzyme or agent is administered as it diffuses out of (is released from) the chamber in the lens or the material of the lens (if the enzyme or agent is soaked into a soft lens). Dosages for different refractive conditions and contact lens delivery vehicles can be optimized through routine experimentation by one of skill in the art.

In accordance with one method of administration through contact lenses of the present invention, corneal hardening enzymes and agents can be applied to the eye through the use of rigid contact lenses. These lenses can be made from known fluoro silicone acrylate lens materials, which are gas permeable. The lens is provided with an internal chamber for storing the corneal hardening enzyme or agent. The chamber preferably comprises a radially symmetrical space encircling the entire lens between the anterior surface and posterior surface of the lens.

Rigid lenses for the present purpose can conveniently be made by lathe cutting, molding, or milling a posterior component and an anterior component from a contact lens button which, during fabrication, can be secured together to form a unitary lens using bonding techniques or adhesives known in the art. The chamber can be formed by lathe cutting an annular recess into the convex surface of the posterior component of the lens before the final lens fabrication. Any of a variety of dimensions can be used in accordance with the present invention, a preferred lens is provided with an annular chamber having a width of approximately 1.0 mm to about 1.5 mm and a depth of from about 0.05 mm to about 0.10 mm.

A plurality of microscopic holes are provided in the posterior portion of the lens to allow fluid communication between the chamber and the eye, thereby facilitating the timed release of the corneal hardening enzyme or agent into the cornea. These holes may be provided by mechanical or laser drilling, or by molding prior to assembling the anterior component and posterior component of the lens. In one embodiment the holes are drilled using a mechanical drill having a microcarbon drill bit.

The pumping action of the eyelids combined with natural tearing assists the release of the corneal hardening enzyme or agent through the tiny holes. Preferably, the holes are produced by mechanical drilling with a microcarbon bit and will have a diameter of from about 0.002 mm to about 0.010 mm, and preferably about 0.005 mm. The number and diameter of the holes can be varied to affect the time release characteristics, as will be apparent to one of skill in the art. In general, however, for the diameter ranges specified above, from about 3 to about 10 holes are contemplated to be used.

In one embodiment of the lens, the posterior portion of the lens has a centerpoint thickness of approximately 0.12 mm and an annular recess is lathed to a depth of about 0.075 mm. A number of holes, each having a diameter of about 0.005 mm, are drilled through the bottom of the chamber and spaced equidistantly apart around the periphery of the chamber to provide communication with the posterior surface of the lens. The number of holes in a lens will vary, depending on the desired rate of administration of corneal hardening enzyme or agent from the chamber.

The anterior portion of the lens, having a centerpoint thickness of about 0.12 mm is thereafter secured to the posterior portion to enclose the annular recess and form a chamber, thereby forming a lens having an overall center thickness of about 0.24 mm. Bonding can be accomplished by applying a small amount of a bonding agent such as Concise™ enamel bonding system sold by 3M (St. Paul, Minn.). Other means of joining the posterior and anterior portions of the contact lens will be apparent to those of skill in the art.

Posterior radii of curvature of the lens are selected that will reshape the anterior corneal curvature to a shape required for rendering the eye emmetropic (no unaided correction). The posterior and anterior configurations of the contact lens in accordance with the present invention are similar to those used in conventional Orthokeratology fitting procedures. In general, the convex anterior surface of the lens approximates a substantially uniform radius of curvature along all planes, and can vary from an aspherical design, a tenticular design, a spherical design, or any other configuration necessary to accommodate the fitting needs of a patient. The concave posterior surface of the lens is divided into several discrete zones, each having a unique curvature. For example, a posterior central base curve may be radially symmetrically disposed about the centerpoint of the lens. An intermediate posterior curvature may be disposed annularly about the radial outer periphery of the posterior central base curve. Adjacent to the radially outward side of the intermediate posterior curvature may be a third peripheral posterior curvature. Thus, the lens can be considered to comprise three distinct zones, a central optic zone, an intermediate zone, and a peripheral zone. Preferably, in accordance with the present invention, an annular chamber may be disposed within the intermediate zone.

In another aspect of the present invention, a contact lens is provided which is composed of two layers which are laminated together. In this advantageous design for a contact lens of the present invention, larger chambers for storing corneal hardening enzyme or agent can be created.

In this contact lens, an anterior portion of the contact lens may be manufactured having an anterior surface and a posterior surface. A posterior portion of the contact lens may also be manufactured with an anterior surface and a posterior surface. The outer perimeter of the posterior surface of the anterior portion may be designed to have the same radius of curvature as the outer perimeter of the anterior surface of the posterior portion. In this way, when the posterior surface of the anterior portion and the anterior surface of the posterior portion are laminated together, a seal may be formed between the outer perimeters of the anterior and posterior portions.

However, in a central portion of the anterior portion, the posterior surface may have a steeper radius of curvature than the anterior surface of a central portion of the posterior portion. Because of this steeper radius of curvature, when the anterior portion and the posterior portion are laminated together, a chamber is formed between the central portion of the anterior portion and central portion of the posterior portion of the contact lens. The volume of the chamber can be adjusted by changing the radii of curvature of the posterior surface of the central portion and of the anterior surface of the central portion, as will be apparent to one of skill in the art.

Prior to manufacture, one or more holes may be made in the central portion of the posterior portion of the contact lens of this design. The holes may be produced by mechanical drilling with a microcarbon bit or by means of a laser such as an argon laser, and will have a diameter of from about 0.002 mm to about 0.010 mm, and preferably about 0.005 mm. The number and diameter of the holes can be varied to affect the time release characteristics, as will be apparent to one of skill in the art. Thus, the rate at which a dose of a corneal hardening enzyme or agent is dispensed from the chamber is largely controlled by the size and number of holes present in the central portion of the posterior portion of the lens. In general, however, for the diameter ranges specified above, from about 3 to about 10 holes are contemplated to be used. These holes may be spaced around the central portion of the posterior portion of the contact lens in order to provide communication between the chamber and the surface of the eye of a subject wearing the lens.

In a preferred embodiment of this lens, the posterior portion of the lens may have a centerpoint thickness of approximately 0.125 mm. The anterior portion of the lens may have a centerpoint thickness of about 0.125 mm. When the anterior portion and the posterior portion are joined, a lens is created having an overall center thickness of about 0.24 mm. If it is desired to change the shape of a cornea with increased rapidity, a lens of increased thickness can be used which exerts more pressure on the cornea to conform to the desired configuration. Bonding can be accomplished by applying a sufficient amount of a bonding agent such as the Concise™ enamel bonding system sold by 3M (St. Paul, Minn.). Other methods of bonding will also be apparent to one of skill in the art.

As with other embodiments of the present invention, concave radii of curvature of the posterior surface of the posterior portion of the lens are selected that will reshape the anterior corneal curvature to a desired shape required for modifying corneal curvature and reducing refractive error. Thus, the posterior and anterior configurations of the contact lens of this aspect of the present invention are similar to those used in conventional Orthokeratology fitting procedures, as previously described and as are known to those skilled in the art.

A lens of this embodiment of the present invention may be made from known fluoro silicone acrylate lens materials. Such rigid lenses can be made by lathe cutting, molding, or milling a posterior component and an anterior component from a contact lens button. After the anterior and posterior components are manufactured, they can be secured together to form a unitary lens using bonding techniques, adhesives, or any other method of attachment known to the art. For example, an enamel bond system can be used to join the anterior and posterior contact lens portions. An example of such a system is the Concise™ enamel bond system sold by 3M (St. Paul, Minn.).

In an alternate embodiment of a contact lens of this aspect of the present invention, a lens is provided which has a peripheral chamber rather than a chamber in the central portion of the lens. In this embodiment, the lens may be composed of an anterior portion and a posterior portion which are laminated together. In this embodiment, a chamber is provided in an intermediate portion of the lens.

In another embodiment, the chamber may be formed in the intermediate portion of the lens by providing an area of the posterior surface of the anterior portion of the lens, which has a steeper radius of curvature than that found in the remainder of the posterior surface of the anterior portion of the lens. As in the foregoing embodiment of a chambered contact lens, the volume of corneal hardening enzyme or agent which can be contained in the lens and thus administered to a subject is largely determined by the radius of curvature of the posterior surface of the interior portion of the lens in the intermediate portion of the lens, as well as by the radius of curvature of the anterior surface of the posterior portion of the lens in the intermediate portion of the lens.

The posterior portion of the lens is also provided with holes through the posterior portion of the lens in the intermediate portion of the lens. These holes serve to allow the transfer of the contents of the chamber from the chamber to the eye of the subject. The number and size of the holes will largely determine the rate at which a corneal hardening enzyme or agent is delivered to the eye.

Although the embodiments of a chambered contact lens have been described as being produced by laminating together an anterior portion and a posterior portion of the lens, one of skill in the art will recognize that other methods of forming the previously described chambers are also possible.

Day and/or night wear of these Enzyme Orthokeratology lenses may be used. The cornea can generally be reshaped in a matter of several hours to a few days. The reshaping progress can be monitored using conventional methods.

The lens of the present invention can be utilized to correct myopia, astigmatism, and hyperopia.

In accordance with a further delivery method of the present invention, a soft lens bandage or shield may be soaked or charged with a dose of the corneal hardening enzyme or agent. The soft lens may then be properly fit to the cornea and worn for a matter of hours to release the enzyme or agent into the cornea. After the enzyme or agent sufficiently hardens the cornea, the soft lens either dissolves or is taken off.

One type of soft lens for use with this method is a collagen material which tends to uptake a relatively high volume of solution containing enzyme or agent and release it relatively slowly. The material may be highly purified bovine collagen. The diameter ranges from about 13.5 mm to about 16 mm. Base curves preferably range from about 8.0 mm to about 9.5 mm. The DK (which is a measure of the oxygen permeability of a material) should be about 50 and the $H_2O$ hydration percentage should be about 83%.

One lens that may be found to be particularly well suited for the practice of this aspect of the present invention is the Medilens™ corneal shield available from Chiron Ophthakimcs, Inc. of Irvine, Calif. The Medilens™ corneal shield is a clear, pliable thin film fabricated from bovine tissue. This tissue has a high percentage of collagen closely resembling the collagen molecules of the human eye.

The Medilens™ corneal shield is stated to provide protection and lubrication to the ocular surface, gradually dissolving within approximately 24 hours. The dry weight of the lens is approximately 5.5 mg, and wet weight following loading with a solution containing an agent or enzyme is approximately 34 mg. Loading is accomplished by soaking the lens in a solution, as previously described, for approximately 60 minutes at room temperature. The uptake of the lens has been measured to be approximately 28.5 mg, and the hydration of the lens is approximately 84%. In volume terms, the uptake of the lens is approximately 200–300 $\mu L$.

Other types of soft lens materials tend to uptake less of a solution containing an enzyme or agent and also to release it more quickly. Examples of such materials are common hydrophilic soft lens materials such as etafilcon A and phemfilcon A, available as ACUCUE from Johnson & Johnson Vision Products, Inc. (New Brunswick, N.J.) and Wesley Jessen (Des Plaines, Ill.). These lenses can be the disposable or long-term wear variety. Lens having an $H_2O$ content of between about 58% and about 70% may be found to be useful in the present method.

Simultaneously or sequentially with release by the soft lens or other delivery vehicle of the corneal hardening enzyme or agent into the cornea, a rigid contact lens is then fit to the cornea. The rigid contact lens rapidly reshapes the treated cornea. A contact lens is used which has a posterior radius that will reshape the anterior cornea to a curvature required for emmetropia. The reshaping process may take from several hours up to a few days.

In one embodiment, the rigid contact lens may be fitted over the central portion of a soft contact lens which has been loaded with a corneal hardening enzyme or agent while that soft contact lens is on the eye of a patient. Due to the intraocular pressure of the eye, the treated cornea will tend to steepen in curvature. While this may be desirable in the case of hyperopia, this should be controlled in treating myopia and other conditions. And even when treating hyperopia, the amount of deepening in corneal curvature should be controlled. Therefore, it may be desirable to place a rigid contact lens over a soft lens which is delivering enzyme or agent in order to control the change in shape of the cornea prior to the time that a rigid lens is fitted directly onto the eye in order to reshape the cornea.

In another embodiment, a rigid lens may be fused to the central portion of a soft contact lens which delivers corneal hardening enzyme or agent to the cornea. In this way, the chances of having errors due to an improper fitting of the rigid lens over the soft lens can be avoided.

In accordance with a further embodiment of the present invention, a saturn-type contact lens, such as the Softperm™ lens sold by Sola Bames Hynds-Pilkington may be utilized. This type of lens comprises a lens with a rigid center and a soft lens peripheral skirt. The rigid, preferably gas permeable center contains no enzyme or agent whereas the soft lens peripheral skirt may be soaked in a solution containing the corneal enzyme or agent.

The peripheral skirt of the satum-type lens may be manufactured from synergicon A copolymer available from Wesley Jessen (Des Plaines, Ill.). The rigid non-hydrophilic center may typically be from about 5.5 mm to 6.5 mm in diameter and has only about 0.2% $H_2O$ absorption. The outer periphery is polymerized into a soft hydrophilic skirt extending circumferentially about the outer periphery of the center and may have a width of from about 3.0 to 4.0 mm, and about 25% $H_2O$ absorption. The base curve of this saturn-type lens ranges from about 7.2 mm to 8.2 mm.

As the saturn-type lens is worn, the corneal hardening enzyme or agent is released into the cornea from the soft peripheral skirt, modifying the cornea in hours. The rigid center of the saturn-type lens immediately begins reshaping the cornea. The rigid center has a posterior radius of curvature that will reshape the anterior cornea to a curvature required for emmetropia as has been discussed. The cornea is reshaped from several hours to a few days. The soft lens skirt gives added comfort and less edge sensation which helps the Orthokeratology process and encourages retainer lens wear.

The corneal hardening enzyme or agent dissipates out of the cornea in a few days while the cornea assumes its new shape. The saturn-type lens or another rigid retainer may preferably worn for a few more days to stabilize the new corneal shape. The lens is then removed.

A "fused soft lens" contact lens system can also be used to release the corneal hardening enzyme or agent into the cornea and simultaneously reshape it. In this embodiment of the present invention, an annular ring of soft lens type material is fused to the inside intermediate curve and peripheral curve of a rigid gas permeable contact lens. The resulting fused (soft) lens is soaked in the enzyme or agent, and the chemical is retained in the soft lens portion. The chemical is then time released into the cornea, which modifies it.

The rigid preferably gas permeable center has a posterior central curvature that reshapes the anterior cornea's curvature to a shape which corrects refractive error, preferably a shape which renders the eye emmetropic. The rigid contact lens center is preferably a fluoro-silicone-acrylate material with a Dk of about 60–92. The diameters vary from about 7.5 mm to 10.5 mm and the base curves of the rigid lens vary from about 7.0 mm to 9.0 mm. The "fused on" soft lens portion is a hydrophilic soft lens material such as etafilcon A or phemfilcon A. Attachment of the annular ring to the rigid contact lens is accomplished by an adhesion process. The width of soft annular ring varies between about 0.75 and 1.5 mm each side.

IV. The Procedure for Use of Hardening Agents in Enzyme Orthokeratology

A. Procedure Generally

The present invention contemplates the use of corneal hardening agents to alter the shape of a subject's cornea from a suboptimal first position to a desired, optimized second position. An Enzyme Orthokeratology contact lens must be properly fit to the surface of the cornea. When the corneal hardening agent is applied, the cornea hardens to lock the proper corneal shape in place.

The Enzyme Orthokeratology method provided herein may include the use of a corneal softening agent. The corneal softening agent aids in altering the shape of a subject's cornea. An Enzyme Orthokeratology contact lens must be correctly fit. When a corneal hardening agent is applied, the cornea hardens to attain the proper corneal shape.

Following hardening of the cornea, the corrective lens is removed and the subject's cornea retains the desired altered conformation. Unlike traditional Orthokeratology methods, the present invention does not require the use of retainer lenses to prevent or inhibit the regression of the cornea to the suboptimal original condition. Also, the time course of treatment of the present invention may be reduced compared to that of other Enzyme Orthokeratology methods. The time course of treatment using the present invention may be shorter since the use of a corneal hardening agent eliminates the need for one to wait for the corneal softening agent to act. Reduction of treatment time may provide increased success rates since the levels of subject participation are minimized.

B. Rigid Contact Lens Design

One preferred embodiment of the rigid contact lenses designed for Enzyme Orthokeratology comprises a lens made of a fluoro-silicone-acrylate material (methylmethacrylate difluoroitaconate siloxanyl copolymer) available from Paragon Optical (Reading, Pa.). The high oxygen permeability of this material DK60–DK151×10–11, allows sleeping in the lens if necessary. The lens also has excellent wettability.

In one preferred lens design, the preferred lens possesses a reverse geometry sculpture. The design constitutes a plurality of curve planes comprising the geometry of the lens which is used to alter the shape of the cornea during the Enzyme Orthokeratology procedure. In one embodiment, the lens contains four curves which comprise the geometry of the lens. In another embodiment, the reverse geometry lenses have two curves steeper than the base curve. The shape and design of these lenses produce the desired results in reshaping a subject's cornea from a suboptimal first position to an optimal second position within hours to days of application.

FIG. 1 shows a plan view of an Enzyme Orthokeratology rigid gas permeable lens 10 for use in treating myopia. The shape of the lens is determined by the deformation of the cornea which is to be corrected. Accordingly, the lenses of the present invention are shaped to correct various corneal irregularities.

The lenses of the present invention use principles of hydrodynamics and a push-pull system to alter the shape of a cornea to a desired conformation. In the embodiment shown in FIG. 1, the flat base curve 12 pushes against and compresses the central cornea into a significantly reduced or longer radius. The central cornea is simultaneously pulled or redistributed into the steep curvature zone 14. The centration curve zone 16 centers the lens and limits the flow of the cornea in response to the forces imposed by the flat base curve and the steep curve. The flat peripheral curve 18 allows for tear exchange and movement of the lens on the surface of the eye.

One preferred embodiment of the rigid contact lenses designed for Enzyme Orthokeratology comprises a lens made of a fluoro-silicone-acrylate material (methylmethacrylate difluoroitaconate siloxanyl copolymer) available from Paragon Optical. The high oxygen permeability of this material allows sleeping in the lens if necessary. The lens has excellent wettability with a low wetting angle.

The flat base curve zone 12 (FIG. 1) corrects the refractive error of the eye to improve unaided visual acuity. Generally the flat base curve (optical zone) 12 diameter ranges from about 6.0 mm to 7.0 mm and is equal to the base cuve in millimeters. The steep curve zone 14 lies outside of the flat base curve zone 12 and has a width range from about 0.6 mm to 0.8 mm. The steep curve zone 14 radius of curvature may be 5 to 10 diopters steeper than the lens base curve depending on the refractive error. Generally, the ratio of the base curvature (BC) to the flattest central corneal curvature(K) in the first conformation (BC/K ratio) multiplied by a factor of 2 determines the steep zone radius of curvature. For example, the lens base curve is fit 4 diopters flatter than the central corneal curvature (BC/K ratio=4 F). The steep zone radius=(BC/K)*2 or 8 diopters steeper than the lens BC. The centration curve zone 16 lies immediately adjacent to the steep curve zone 14 and the range of this zone varies from about 0.8 to 1.0 mm. Generally, the curvature of the centration curve zone 16 will equal the curvature of the base curve zone 12 plus two to three diopters. The peripheral curve zone 18 is flatter than the base curve 12 of the lens. The width of the peripheral curve zone 18 varies from 0.4 mm to 0.5 mm. The peripheral curve zone 18 allows for tear circulation and oxygen exchange during blinking.

The total diameter of the lens is determined by the base curve diameter plus the steep zone plus the centration zone to the peripheral curve. The lens diameter ranges from about 10 mnm to 13 mm.

The power of the lens is based on the refractive error of the patient and the lens base curve to central corneal curvature relationship. Generally the lens thickness is 0.24 mm for 0 power; 0.01 mm should be subtracted for each diopter of minus correction, and 0.02 mm should be added for each diopter of plus. The concave posterior curvature of the flat base curve zone 12 is preferably calculated to reshape the cornea from a suboptimal first conformation to an optimal second conformation, thus making the eye emmetropic when the cornea is molded to this curvature. The front curvature of the flat base curve zone 12 is of a radius calculated to give the subject no refractive error and 20/20 aided visual acuity while wearing the lens. All of the rigid contact lens parameters vary depending upon the refractive error, corneal curvature and size, and fitting formula, as is known in the art.

A further embodiment of a rigid contact lens designed specifically to be used in the treatment of hyperopia is contemplated. Such a contact lens should be rigid, such as the previously described lenses made from a fluoro-silicone-acrylate material. In this embodiment, the concave (posterior) portion of the lens may be a spheric or an aspheric base curve. A central portion of the lens is formed so that the concave surface of the central portion is shaped so as to produce emmetropia. This central portion has a base curve may be 1–5 diopters steeper than the central corneal curvature. The peripheral curves are much flatter than standard contact lenses and the diameters are larger. The steeper base curve of the lens is designed to steepen the central corneal curvature to reduce hyperopia and improve near and far unaided visual acuity.

In an alternative lens design, the rigid contact lenses contemplated for Enzyme Orthokeratology comprises a lens made of a fluoro-silicone-acrylate material (methylmethacrylate difluoroitaconate siloxanyl copolymer) available from Paragon Optical. The high oxygen permneability of this material DK60–DK151×10–11, allows sleeping in the lens if necessary. The lens has excellent wettability with a low wetting angle. The base curve of the lens varies from 6.5 mm to 9.0 mm, depending upon the central corneal curvature. The total diameter of the lens is the base curve in mm +1.3 mm to 2.0 mm, and the range is about 7.5 mm to 15 mm.

The central optic zone is transparent and corrects the refractive error of the eye to produce excellent visual acuity. The optic zone diameter ranges from 6.5 mm to 9.0 mm. The intermediate zone contains a chamber for enzyme or agent to release the solution into the cornea. The width of the intermediate zone varies from 0.35 mm to 1.0 mm. The intermediate curve may be steeper or flatter than the base curve of the lens depending on the refractive error. The peripheral curve is flatter than the base curve of the lens. The width of the peripheral zone varies from 0.35 mm to 1.0 mm. The peripheral curves allow for tear circulation and oxygen exchange during blinking.

The power of the lens is based on the refractive error of the patient and the lens base curve to central corneal curvature relationship. The thickness is 0.24 mm for 0 power; 0.01 mm should be subtracted for each diopter of minus correction, and 0.02 mm should be added for each diopter of plus. The concave posterior curvature of the optic zone (base curve) is preferably calculated to make the eye emmetropic when the cornea is molded to this curvature. With myopia the base curve is fit 1–3 diopters flatter than the central corneal curvature. This may be accomplished with one to three lenses. The front curvature of the optic zone is of a radius calculated to give the subject no refractive error and 20/20 aided visual acuity while wearing the lens. The final lens will have zero refractive power. All of the rigid contact lens parameters vary depending upon the refractive error, corneal curvature and size, and fitting formula, as is known in the art. This lens design may also be used unloaded to reshape the cornea.

A further embodiment of the rigid contact lens design for use in the treatment of astigmatism. With astigmatism, the cornea exhibits an unequal curvature, (i.e., flatter curvature in one meredian and steeper curvature in the opposite meridian.) In one lens design, an aspheric base curve and peripheral curves are used to reshape the cornea to a more spherical shape. The lens has a uniform eccentricity change which reduces the curvature in the steeper meridan. This feature sphericalizes the cornea, reduces the astigmatism, and irnporves unaided visual acuity.

A second design incorporates a toric base curve with base prism to orientate the steepr and flatter curves of the lens in the proper direction to correct the unequal curvature of the cornea. The lenses of this embodiment are constructed of similar materials as described above, however, 60–92 DK lenses are preferred.

Yet another embodiment of a rigid contact lens is designed specifically to be used in the treatment of hyperopia. Such a contact lens should be rigid, such as the previously described lenses made from a fluoro-silicone-acrylate material. In this embodiment, the concave (posterior) portion of the lens is formed with a peripheral portion which has an aspheric base curve. A central portion of the lens is formed so that the concave surface of the central portion is shaped so as to produce emmetropia. This central portion has a base curve which is 1–5 diopters steeper than the base curve of the peripheral portion of the lens, and has a radius of curvature which is up to 1 mm steeper than the peripheral portion. The base curve of the central portion of the lens may also be designed to produce a desired radius of curvature of a cornea which does not render the cornea emnmetropic, but which still steepens the base curve of the cornea.

C. Myopia Enzyme Orthokeratology Procedure

Myopia is a condition in which, typically, the shape of the eye is elongated, resulting in the focusing of parallel light rays in front of the retina. A corrective lens is used in this procedure that has a base curve flatter than that of the central corneal curvature up to the amount of the myopia in diopters. The inner radius of the intermediate zone may be up to 8 diopters steeper than the base curve. The steeper central corneal curvature is reshaped to a flatter curvature and the flatter paracentral curvature is reshaped to a steeper shape. The result is a spherical cornea from center to paracentral with a flatter central curvature. This eliminates myopia because the light is refracted farther back on the retina instead of in front of the retina, and there is less spherical aberration.

As will be apparent to one of skill in the art, a number of other lens designs can be used in treating myopia which have varying diameter base curves and thicknesses. Included in such designs are contact lenses having aspheric base curves and peripheral curves and those having spherical base curves and aspheric peripheral curves.

The following example illustrates a method for correcting myopia using Enzyme Orthokeratology of the present invention. In this example, a patient exhibits 20/300 uncorrected visual acuity (UVA) or 3 diopters myopia; a flattest central curvature of 45 diopters or 7.5 mm; and a paracentral curvature of 40 diopters and the cornea is positively shaped at +0.30. The patient is treated according to the methods of the present invention.

Using the above-described methods, an appropriate concentration of glyceraldehyde was determined for use in the present invention. In one embodiment, a range of glyceraldehyde concentrations from about 0.1% to 5.0% are contemplated for use in the present invention. In another embodiment, a range of concentrations from about 1% to 4% are further contemplated. Finally, in still another embodiment, use of a glyceraldehyde solution of about 3% to induce corneal cross linking is contemplated y the present invention.

A corneal-hardening amount of a corneal hardening agent is administered to the patient. One such agent is a 3% glyceraldehyde solution. The 3% glyceraldehyde solution is prepared under sterile conditions by dissolving 1.5 grams of glyceraldehyde into 50 mL of 0.9% sodium chloride USP. This solution is then sterile filtered and aliquoted. The route of administration may include a sole intrastromal injection, or it may consist of topical applications to the corneas of the subject.

In an embodiment where an intrastromal injection step is used, subjects receive a single corneal intrastromal injection of about 20 $\mu$L of a 3% glyceraldehyde solution using an appropriate injection technique. For example, the subject is administered an optical anesthetic such as a 0.5% proparacaine solution (Bausch and Lomb, Tampa, Fla.). The eye to be injected is gently proptosed and the syringe needle is gently introduced into the supertemporal quadrant into the corneal stroma. The hardening agent is then injected as a single bolus into the corneal stroma. Upon injection, the hardening agent cross links corneal components for a period of time, from minutes to days, as appropriate, hardening the cornea.

Application of a 3% glyceraldehyde solution may alternatively be performed through eye drops at one to four drops from one to four times daily. The 3% glyceraldehyde solution is applied in a dropwise fashion to the treated corneas. The procedure used entails gently tilting the subject's head to allow the drop to fall on the cornea and not adjacent structures, holding the upper eyelid open, applying a drop of the solution to the eye of the subject, and allowing the subject to blink. The administration of the corneal hardening agent may occur hourly or daily from one to one hundred (100) days.

Rigid gas permeable corrective contact lenses are fitted to the eyes of the subject to mediate corneal reshaping. The corrective lens provides a scaffold upon which the cornea may be reshaped into the desired second configuration. The dimensions of the corrective lenses used in the treatment are determined by the deformation of the subject's eyes as determined by standard diagnostic techniques known to one skilled in the art. The corrective lenses in this example have a base curve of 42 diopters or 8.0 mm (3 diopters flatter than central curvature). The optic zone width is 8.0 mm. The power of the lens is piano (0). The size of the lens is 9.6 mm (8.0+1.6 mm). Its thickness is 0.20 mm. The intermediate curve radius is 7.5 mm or 45 diopters (3 diopters steeper than the case curve) with a width of 0.50 mm. The peripheral curve has a radius of 10.0 mm, with a width of 0.30 mm.

In another embodiment of the present invention, the lens is loaded with a dose of corneal hardening agent. The contact lens is properly fitted to the cornea and the agent is released into the cornea over the course of from a few minutes to a few days, as appropriate. The enzyme penetrates into the stroma where it hardens the connective tissue layer. The treated cornea reshapes its anterior central curvature (45 diopters) to the posterior base curve of the lens (42 diopters). The cornea's new anterior central curvature becomes 42 diopters (3 diopters flatter than its original 45 diopters). The paracentral anterior cornea (40 diopters) steepens to 42 diopters=8.0 mm. The cornea now has a spherical shape. The original three diopters of myopia are now reduced to no correction (plano or emmetropic), and unaided (natural) visual acuity is improved to normal 20/20 from 20/300.

Before, during, and after treatment, a patient's optical health may be monitored. Monitoring methods include standard physical examinations performed by one skilled in the art. Additionally, slit lamp biomicroscopy may be used to assess a patient's optical health. A slit lamp such as a Nikon FS-2 Slit Lamp may be used for the subject's examination. Such an examination might include the steps of dilated the eyes of the subject by instilling one drop of 1.0% tropicamide (Bausch and Lomb, Tampa, Fla.) and 2.5% phenylephrine (Bausch and Lomb, Tampa, Fla.). Following dilation the subject is then positioned in front of a slit lamp and examined for edema. The anterior chambers of the subject may then be examined for chamber depth, aqueous cell and flare, and fibrin. The iris of each subject may be examined for atrophy, symmetry, or synechiae. The lenses may also be examined for the presence of cellular debris, capsule, or lens protein abnormalities. The vitreous humor of each may also be examined for the presence of cells or other abnormalities. Finally, Fluress (topical fluorescein) (Akorn Pharmaceuticals, Abita Springs, La.) may be instilled to examine the subjects for any epithelial defects that might be present.

In this case, the application of the corneal hardening agent acts to cross link amino acid residues in the collagen of the stroma, which in turn results in an increase in corneal rigidity. Since corneal hardening takes place while the cornea is held in the desired second conformation by the lens, the hardened cornea hardens in the desired second configuration. As a result of application of the hardening agent, the treated corneas retain the proper shape upon removal of the corrective lenses.

In an alternate embodiment of the Enzyme Orthokeratology procedure described above, a corneal softening amount of a corneal softening agent is administered prior to addition of a corneal hardening agent. For example, 500 international units (IR) of hyaluronidase is administered by intrastromal injection into a subject's eyes. The hyaluronidase is manufactured as a sterile lyoplulized product and packaged in vials, each containing 6,000 IU of a highly purified hyaluronidase (Biozyme, Blaenavon, UK). In addition to the enzyme, the product may include 1.22 mg potassium phosphate, monobasic; 1.92 mg potassium phosphate, dibasic; and 5 mg lactose. Within three hours of intended use, the vials are reconstituted with 0.24 mL of 0.9% sodium chloride USP and 20 $\mu$L is drawn up into syringes to deliver the desired 500 IU. A suitable syringe for use in this method is a 0.3 cc insulin syringe fitted with a half-inch 29-gauge needle (Becton-Dickinson, Franklin Lakes, N.J.) or its equivalent. Upon injection, the corneal softening agent hydrolyzes the carbohydrate substrate for a period of time, from minutes to days, as appropriate, softening the cornea and preparing it for reshaping. At this point, the corneal softening agent is allowed to dissipate or its activity is inhibited, and a corneal hardening procedure is followed to achieve a desired corneal shape.

D. Astigmatism Enzyme Orthokeratology Procedure

Astigmatism is a refractive error of the lens system, caused usually by an oblong shape of the cornea. In this condition, the central corneal curvature is uneven, resulting in a stretching of the image on the retina. The horizontal and vertical central meridians are of different curvatures. The astigmatism contact lenses may use toric and aspheric base curves, intermediate curves, and peripheral curves that may incorporate prism and/or truncation. The initially flatter central meridian of the eye is reshaped to take on a steeper curvature and the initial steeper curvature and the initial steeper central meridian is reshaped to take on a flatter curvature. This process reshapes the central corneal curvature to a spherical shape and eliminates astigmatism.

To correct astigmatism using Enzyme Orthokeratology, the following procedure is used. In one embodiment of the present invention, the material for the lens is fluoro-silicon-acrylate. The base curves (6.0 mm–8.5 mm) may be back toric, front toric, or bitoric. The flattest central corneal curvature is aligned with a steeper base curvature. The steeper central corneal curvature is aligned with a flatter base curvature. Aspheric or spherical base curves and peripheral curves may also be used. The lens diameter is the base curve in mm +1.3 to 1.8 mm. The range is from about 7.5 mm to about 11.5 mm. The optic zone diameter equals the base curve in mm and ranges from about 6.5 to about 9.5 mm. The intermediate curve radius ranges from about 1 diopter to about 2 diopters flatter than the base curve. The width is from about 0.35 to about 1.0 mm. The peripheral curves range from about 2 to about 4 diopters flatter than the base curve. The width is 0.35 to 1.0 mm. The intermediate and peripheral curves may be aspheric. Prism and/or truncation is used to keep the lens aligned in the proper position to reshape the astigmatic cornea.

The thickness of the lens varies with lens power. If zero lens power=0.20 mm, subtract 0.01 mm for each diopter of minus and add 0.02 mm for each diopter of plus power. The power of the lens is computed based on the patients refractive error and the base curve/corneal curvature relationship. The astigmatic lenses may be loaded with a corneal hardening agent or enzyme as a delivery vehicle, or the lens design may be used unloaded to reshape the cornea.

E. Hyperopia Enzyme Orthokeratology Procedure

Hyperopia results from a suboptimally short distance from the surface of the eye to the retina. To correct hyperopia the central curvature of the cornea must be reshaped to a steeper curvature. The light entering such an eye requires greater refraction since the image projected through the cornea is focused behind the retina and needs to be moved forward onto the retina. The lens base curve may be fitted steeper than the central corneal curvature with flatter aspheric intermediate and peripheral curves. A hole in the center of the lens may be used to encourage and give the space for the central cornea to steepen. Alternatively, a contact lens as described hereinabove may be used to correct hyperopia.

To correct hyperopia using Enzyme Orthokeratology, the following procedure is used. In one embodiment of the invention, a fluoro-silicone-acrylate material is used for the lens. A hole ranging from 2.5 mm to 4.5 mm diameter is provided in the center. The base curve of the lens is fit steeper than the central corneal curvature. The corrective lens possesses a corrective curvature wherein the base curves vary from 5.5 mm to 8.0 mm and the diameter is the base curve in mm +1.0 mm to 1.5 mm (6.5 to 9.5 mm range). Smaller diameters are used because the curvature of the lenses is steeper than that of the central cornea. The intermediate and peripheral curves should be aspheric curves 1 to 3 diopters flatter than the base curve. The width of these curves is 0.35 mm to 1.0 mm. The optic zone is between 5.5 mm to 8.0 mm. The thickness of the lens is dependent upon the power necessary for correction. With hyperopia the lenses will be thicker. If the power is plano (0) the thickness=0.20 mm, then add 0.02 for each diopter of plus. The power of the lens is computed based on the patient's refractive error adjusted for the base curve/corneal curvature relationship. The hyperoptic lenses may be loaded with a corneal hardening agent or enzyme as a delivery vehicle, or the lens design may be used unloaded to reshape the cornea.

V. Other Therapeutic Uses of Enzyme Orthokeratology

The present methods of reshaping a cornea can be used to effect therapeutic benefits other than correcting refractive errors. Additional therapeutic benefits include improving corneal smoothness, improving or rehabilitating corneal irregularities and stabilization of corneal structures.

One contemplated use of the present invention is to rehabilitate irregularities and improve refractive errors that result from various corneal surgeries including photorefractive keratectomy (PRK)(an example of which is described in U.S. Pat. No. 5,699,810), LASIK (an example of which is described in U.S. Pat. No. 5,697,945), radial keratotomy (RK)(an example of which is described in U.S. Pat. No. 5,611,805), thermokeratoplasty, photothermokeratoplasty (examples of which are described in U.S. Pat. Nos. 5,749,871 and 5,779,696), corneal transplant surgery, and cataract surgery.

For example, photorefractive keratectomy (PRK), is an extremely common procedure worldwide. The present invention could be used to preserve and stabilize the surgical reshaping of the cornea post-operatively. In this embodiment, a patient who had undergone the PRK procedure would be identified and an acceptable corneal hardening agent would be selected. Following the application of stabilizing contact lenses, the patient would be administered a corneal hardening amount of the the corneal hardening agent. The contact lenses and the application of the hardening agent would remain on the patient's eyes for a suitable period of time so as to assure the stabilization of the surgically reshaped cornea. The same treatment would be applicable to patients who had received LASIK or RK.

Similarly, the present invention may also improving the chances of success for other corneal procedures, such as corneal transplant surgery and cataract surgery. One of the most common reasons for the clinical failure of surgical procedures like corneal transplants, for example, is the existence of residual refractive error such as irregular astigmatism following an otherwise successful surgery. The present methods could be used to correct the refractive error that occurs as a result of disease, surgery, or other conditions. Also, the present invention may also promote faster healing and allow early removal of sutures, which are usually left in place for 6 to 12 months. Increased healing is promoted by post-operative corneal hardening since this hardening diminishes the need for sutures.

The present invention may also be efficacious in treating a number of corneal pathologies that result in corneal irregularities. Diseases or conditions of the cornea such as keratoconus, corneal melting disorders, corneal ulcers, recurrent corneal erosions, pterygium may be treatable using the methods of the present invention. Also, contact lens-induced corneal warpage, contact lens intolerance and contact lens induced erosions might also be combated by stabilizing and hardening the cornea using the corneal hardening agents of the present invention.

To use the foregoing methods of the present invention to effect these further clinical benefits, subjects who have an irregularly shaped cornea or who have under gone a corneal manipulation are first identified. Such identification is normally accomplished by an eye specialist or other practitioner skilled in the art who can diagnose an individual as having an irregularly shaped cornea or having undergone corneal manipulation. The previously described methods of Enzyme Orthokeratology are then used to reshape the cornea of the individual to a desired configuration.

The following examples illustrate embodiments of the present invention. Such examples are illustrative only and not meant to limit the scope of the present invention.

EXAMPLE 1

Safety of Glyceraldehyde Delivered by Topical Ophthalmic Drops and Corneal Intrastromal Injections In this Example, the safety of treating Dutch Belted rabbit corneas with glyceraldehyde following administration of the corneal softening enzyme hyaluronidase was investigated. This study involved the use of five (5) pigmented Dutch Belted rabbits, two (2) in the control group and three (3) in the glyceraldehyde treated group.

All rabbits received a thorough slit lamp examination on the first day of the study to establish the baseline using the following technique. A Nikon FS-2 Slit Lamp was used for the examinations of the test animals. For each animal examined, the eyes were dilated by instilling one drop of 1.0% tropicamide (Bausch and Lomb, Tampa, Fla.) and 2.5% phenylephrine (Bausch and Lomb, Tampa, Fla.). The animal was then positioned in front of a slit lamp. The corneas of each animal were examined for edema and the surface area involved with edema was estimated. The anterior chambers of the animals were closely examined for chamber depth, aqueous cell and flare, and fibrin. The iris of each animal was examined for atrophy, symmetry, or synechiae. The lens was examined and cellular debris, capsule, or lens protein abnormalities were noted if present. The vitreous humor of each animal were then examined for the presence of cells or other abnormnalities. Finally, Fluress (topical fluorescein) (Akom Pharmaceuticals, Abita Springs, La.) was instilled to the examined animals and epithelial defects were noted if present.

The following scoring system was used to evaluate the experimental animals.

A. Cells and Flare (C/F)
   0—no cells observed
   trace—1 to 5 cells observed per slit beam field
   +1—5 to 10 cells observed per slit beam field
   +2—10 to 20 cells observed per slit beam field
   +3—20 to 50 cells observed per slit beam field
   +4—greater than 50 cells observed per slit beam field
B. Corneal Edema/Haze
   0—no edema/haze observed
   trace—faint opacification of the cornea, still able to see fine details of the iris
   +1—mild opacification of the cornea, still able to see most details of the iris
   +2—moderate opacification of the cornea, able to see large details of the iris
   +3—severe opacification of the cornea, able to see iris, though without details
   +4—complete opacification of the cornea, unable to see the iris
C. Iris Synechiae
   0—no synechiae seen
   1–12—corresponds to the number of clock hours of synechiae observed with each clock hour corresponding to approximately 30° of iris involvement
D. Lens
   0—no opacification (i.e. cataract) or mechanical defect (possibly secondary to procedural trauma) present
   1–12—cataract or lens defect observed (these observations have not been qualitatively assessed)
E. Vitreous Cells
   0—no vitreous cells seen
   trace—1 to 5 cells observed per slit beam field
   +1—5 to 10 cells observed per slit beam field
   +2—10 to 20 cells observed per slit beam field
   +3—20 to 50 cells observed per slit beam field
   +4—greater than 50 cells observed per slit beam field
F. Fibrin
   0—no fibrin seen
   trace—1 thin, delicate strand identified
   +1—1 thick or 2–3 thin, delicate strands present
   +2—2 thick or more than 3 thin, delicate strands present
   +3—multiple strands of various size present
   +4—thick, opaque, 3-dimensional strands of fibrin present
G. Epithelial Defects
   N—no epithelial defect
   SPK—superficial punctate keratopathy—more than three minutes (<0.3 mm) lesions staining
   F—focal epithelial defect—a larger (>0.3 mm) patch of staining Subsequent to this baseline examination, all rabbits received 500 IU of a hyaluronidase formula bilaterally into the corneal stroma on Study Day 1. The hyaluronidase formula was prepared as follows. The formula was manufactured at Prima Pharm, Inc. (San Diego, Calif.) as a sterile lyophilized product and packaged in vials, each containing 6000 IU of a highly purified hyaluronidase. In addition to the enzyme there was included: 1.22 mg potassium phosphate, monobasic, 1.92 mg potassium phosphate, dibasic, and 5 mg lactose. Within three hours of intended use, the vials were reconstituted with 0.24 mL of 0.9% sodium chloride USP and 20 $\mu$L were drawn up into syringes to deliver the desired 500 IU. The syringes used were 0.3 cc insulin syringes fitted with a ½ inch 29-gauge needle (Becton-Dickinson, Franklin Lakes, N.J.) or their equivalents.

The hyaluronidase formula was administered by corneal intrastromal injections. First the animals were anesthetized with ketamine 30 mg/kg and xylazine 7 mg/kg. The animals were then placed on an examination table and administered two (2) drops of proparacaine 0.5% (Bausch and Lomb, Tampa, Fla.), an optical anesthetic. The eye to be injected was gently proptosed and the syringe needle gently introduced into the superotemporal quadrant into the corneal stroma. The full 20 $\mu$L was then injected as a single bolus into the corneal stroma. Following the injections, the rabbits were returned to their cages for recovery. The rabbits received no further manipulations except for examinations and care until Study Day 8.

The administration of the test agents began on Study Day 8. The control animals were administered a Balanced Saline Solution (BSS) (IOLAB Corporation, Claremont, Calif.) three times daily in both eyes. The experimental animals received a single corneal intrastromal injection of 20 μL of 3% glyceraldehyde solution using the injection technique discussed above. The glyceraldehyde solution was prepared under sterile conditions at Prima Pharm by dissolving 1.5 grams of glyceraldehyde in 50 mL of 0.9% sodium chloride USP, sterile filtering, and aliquotting the solution.

Subsequent administrations of the BSS to the control animals or glyceraldehyde solution to the experimental animals were made through eye drops. The experimental rabbits received one drop of glyceraldehyde solution three times a day. The procedure used entailed removing the animals from their cages, gently tilting the animal's head to allow the drop to fall on the cornea and not adjacent structures (e.g., eyelids, etc.), holding the upper eyelid open, applying 1 drop of the solution to the eye of the test animal, and allowing the animal to blink. Balanced Saline Solution was administered to the control group animals in an analogous fashion. The rabbits receiving topical drops received glyceraldehyde or BSS for a total of 50 days.

Data was collected from the animals on Study Days 1 (baseline), 2, 4, 8 (before and 4 hours after injection), 9, 11, 16, 22, and 31. The animals received a thorough slit lamp examination and the criteria discussed above was documented.

The animals were sacrificed and their eyes were harvested on Study Day 58. The animals in the study were euthanised using an intravenous injection of pentobarbital (2 mg/kg). The eyes of the animals were enucleated immediately after sacrifice using Castro-Viejo scissors. The corneas of the eyes were then removed and placed on the end of a glass tube and cut in half. These samples were then snap frozen in liquid nitrogen. The corneas were transported to a facility possessing a cryostat on dry ice and embedded in O.C.T. embedding compound (Miles Labs, Elkhart, Ind.). The corneas were then sectioned, stained with hematoxylin/eosin and the slides were sent to a Board-certified Veterinary Pathologist for interpretation.

The data was analyzed and any abnormalities seen on the clinical examination were converted to numerical scores as follows:

| Finding | Score |
|---------|-------|
| normal  | 0     |
| trace   | 1     |
| +1      | 2     |
| +2      | 3     |
| +3      | 4     |
| +4      | 5     |

Synechiae were scored by a clock hour system where each integer corresponds to the number of clock hours (30 degrees) of synechiae observed (i.e. 0=normal, 12=360 degrees of involvement). Epithelium, conjunctiva and lens criteria were scored as normal=0 and abnormal=1.

Although the statistical power of the study was small with only two and three rabbits in the control and treatment groups respectively, a statistical analysis were performed. The group's means for each clinical score were compared using a student's t-test assuming equal variances.

The statistical analysis of the clinical observations showed no differences between the groups of animals.

Histopathologic examinations of the harvested corneas showed widespread vacuolization of cells contained therein. This result was considered an artifact possibly due to the snap freezing and subsequent tissue processing of the harvested corneas. In light of this observation the methods used for tissue fixation and processing used in Example 2 were changed. However, it should be noted that there were no appreciable differences noted by the reviewing pathologies between the corneas of the control and treated groups.

EXAMPLE 2

Safety of Glyceraldehyde Use in Hyaluronidase Treated and Untreated Eyes Including Evaluation of Corneal Epithelial Viability and Indirect Ophthalmoscopy This example further examines the safety of glyceraldehyde treatment in an animal model. The experiment described in Example 2 involved the study of six (6) pigmented Dutch Belted rabbits, two (2) in the control group and four (4) in glyceraldehyde treated experimental group. On Study Day 1, all rabbits received a thorough ophthalmic examination including slit lamp biomicroscopy and indirect ophthalmoscopy.

The slit lamp biomicroscopy was performed substantially as described in Example 1. However, Rose Bengal stain was used here applied using Rose Bengal Ophthalmic Strips (Barnes-Hind, Inc., Sunnyvale, Calif.). This procedure involved a sterile strip wetted in 0.9% sodium chloride applied to the extraocular muscles and sciera of an examined rabbit. The rabbit was allowed to blink applying the stain and then the treated eye was examined. Slit lamp biomicroscopy including Rose Bengal staining was performed on Study Days 1 (baseline), 8, 9, 11, 15, 34, 45, and 63. The animals were scored and the results recorded using the criteria described in Example 1.

The indirect ophthalmoscopy was performed using a Heinz Indirect Ophthalmoscope with a 20 D hand lens. First, the eyes of an animal to be examined were dilated with a solution of 2.5% phenylephrine and 1.0% tropicamide (Bausch and Lomb, Tampa, Fla.) as described in Example 1. The examination room was darkened and the animal to be examined was transferred to a examination table. The 20 D lens of the indirect ophthalmoscope was cleaned and the headlamp adjusted such that the lamp focuses just inferior to the horizontal meridian of the examiner. The inferior vitreous and retina were examined first, sweeping to cover the nasal and temporal periphery. The examiner then moved far temporally and examined the peripheral retina and vitreous sweeping inferiorly and superiorly. The examiner then moved far nasally and repeated the up-down sweep. The superior retina, optic disc, and vitreous were also examined. Lastly, the mid-retina and vitreous were examined. Any scars, detachments, irregularities, hemorrhages, or other abnormalities were noted for each animal. Indirect ophthalmoscopy was performed on Study Days 1, 34, and 63.

Following baseline examinations, the rabbits were anesthetized and received a corneal intrastromal injection of 500 IU of hyaluronidase in OD (right eye) only using the method described in Example 1.

The administration of the test agents in the form of topical eyedrops began on Study Day 8. The control animals were administered a Balanced Saline Solution (BSS) (IOLAB Corporation, Claremont, Calif.) four times a day in each eye.

The experimental animals received a 3% glyceraldehyde solution. The glyceraldehyde solution was prepared under sterile conditions at Advanced Corneal Systems (Irvine, Calif.) by dissolving 18 grams of glyceraldehyde in 600 mL of 0.9% sodium chloride USP, sterile filtering, and aliquotting the 3% glyceraldehyde (w/v) solution into 10 ml droppers. The experimental rabbits received one drop of glyceraldehyde solution four times a day using the technique described in Example 1. The rabbits received topical drops for a total of 63 days.

On Study Day 71 (following 63 days of drops), corneal scrapings were performed as follows. Photographs of the uninstrumented eyes were taken after fluorescein staining. Fluorescein staining was performed as described in Example 1. The examined animals were then placed under general anesthesia using ketamine/xylazine also as described in Example 1. Two (2) drops of proparacaine were instilled into both eyes of the examined animal as an anesthetic. The animal to be examined was then placed on an examination table with one eye gently proptosed. A 10×15 mm strip of epithelium from the central cornea was denuded with a sterile #11 scalpel blade (Feather Safety Razor Co., Ltd., Japan). The examined animal was then returned to the slit lamp, topical fluorescein was applied, and the eye was photographed. The animals were examined for reepithelialization at 1, 2, and 3 days post-scraping. Photographs were taken and the rate of re-epithelialization was determined and documented.

The study animals were sacrificed on Study Day 74 with an intravenous injection of pentobarbital (2 mg/kg). Eyes from the study animals were enucleated immediately post-sacrifice and placed in labeled tubes containing approximately 5 mL of half-strength Karnovsky's fixative (2.5% glutaraldehyde, 2.5% paraformaldehyde, 2.5 mM $CaCl_2$, 100 mM Na Cacodylate, pH 7.4) for approximately 1 hour. The eyes were removed and small windows (1×3 mm) were made in the cornea/iris to allow penetration of the fixative to the vitreous. The eyes were then placed in 25 mL of fresh fixative. The fixed eyes were then sent to Consolidated Veterinary Diagnostics, Inc. (West Sacramento, Calif.) where they underwent routine tissue processing, sectioning, and staining with hematoxylin/eosin. They were examined by a Board Certified Veterinary Pathologist.

Evaluation of the data indicates that glyceraldehyde treatment of the eyes produced no significant changes to the structure of the eyes as compared to controls. This conclusion is supported by the observed presence of aqueous cell and flare in the experimental animal group. Baseline examinations of the study animals indicated that the glyceraldehyde treated cohort had aqueous cell and flare and that the control animals did not. However, the data indicate that the animals improved over time and cell/flare was absent by day 14. These results suggest that the administration of glyceraldehyde to the test animals did not appear to impair the resolution of the cell and flare.

Furthermore, baseline examinations using indirect ophthalmoscopy revealed no abnormalities beyond a few scars and areas of mottled pigmentation of the retina which remained unchanged throughout the study.

Additionally, the scraped corneas of the glyceraldehyde treated animals healed at a rate equivalent to those of the control (BSS) treated eyes.

The eyes which had undergone corneal scraping and a subsequent healing period were sent to Consolidated Veterinary Diagnostics for tissue processing and pathologic interpretation. In toto, 4 eyes from the glyceraldehyde treated group and 2 eyes from the BSS group were evaluated. One of the two control (BSS) eyes had a focus of stromal change described as an increased number of stromal nuclei and nuclear fragmentation in the subepithelial stroma near the limbus. This description would imply a response to injury (presumably the scraping). One of the four glyceraldehyde treated eyes had a superficial scar in the corneal stroma and disruption of Bowman's membrane (also presumably due to scraping).

EXAMPLE 3

Large-scale Safety Study Under Good Laboratory Practices Conditions

Example 3 describes a large scale study of twenty-seven (27) pigmented Dutch Belted rabbits to demonstrate the safety of the 3% glyceraldehyde treatment. This study was conducted in compliance with the Good Laboratory Practices requirements of the U.S. Food and Drug Administration. Here, 27 eyes were randomly chosen to form the control group and the remaining 27 eyes formed the experimental group. All of the animals received ophthalmic examinations consisting of slit lamp biomicroscopy (as described in Experiment 2) and intraocular pressure measurements (IOP) as generally practiced in the art, before the experiment began to establish baseline conditions.

Following baseline examinations, all rabbits received 500 IU in 20 μL of hyaluronidase into the corneal stroma bilaterally using the injection method described in Experiment 1. No examinations or treatments were performed on the animals until Study Day 8. On Study Day 8, the animals received slit lamp examinations and IOP measurements.

Treatment with topical eyedrops began immediately after the Day 8 examinations. Each rabbit received 2 drops of test agent four times a day at 05:00, 09:00, 13:00 and 17:00. The 3% glyceraldehyde solution was prepared in 0.9% sodium chloride USP under Good Manufacturing Practices (GMP). The 0.9% sodium chloride for injection was also prepared using GMP. Each rabbit eye in the experimental group received the 3% glyceraldehyde solution while the control eyes received a 0.9% sodium chloride solution. Animal care givers were not informed as to the treatment scheme. The contract animal testing facility instilled the eyedrops using the method described in Experiment 1, in accordance with GLP. The rabbits received 2 applications of the specified test agent in each eye for a total of 32 days.

The animals were examined using slit lamp biomicroscopy and intraocular pressure measurements were taken on Study Days 1 (baseline), 8, 9, 12, 15, 22, and 40.

On Study Day 40, after 32 days of drops, the animals were sacrificed and the eyes were harvested according to the methods described in Experiment 2. The eyes were fixed in half-strength Karnovsky's fixative as described in Experiment 2 and sent to a Board Certified Veterinary Pathologist for interpretation.

Intraocular pressure (IOP) measurements were made. Statistical analysis of IOP measurements included analysis of the mean IOP values in millimeters of mercury (mm Hg). Additionally, in order to normalize for the baseline variations in intraocular pressure, IOPs were converted to a percentage of the original (baseline) pressure using the following formula: (measurement on given examination day (mm of Hg)/baseline measurement (mm of Hg))*100. These means were then compared in a paired t-test.

Many of the indices of host response/toxicology were completely normal for all 20 eyes examined over all seven (7) timepoints documented. None of the 14 criteria (conjunctiva, corneal edema score, corneal edema % surface area involved, Rose Bengal Score, Rose Bengal % surface area involved, epithelial defects, superficial punctate keratopathy score, superficial punctate keratopathy % surface area involved, aqueous cell and flare, fibrin, iris abnormalities, lens abnormalities, vitreous cells, or intraocular pressure) demonstrated statistically significant differences between the control and glyceraldehyde treated groups for any timepoint.

The histopathology results of this experiment showed a minimal to mild lymphoplasmacytic infiltrate of the corneal stroma at the limbus which is commonly seen in rabbits. There was also minimal to mild acute conjunctivitis attributable to terminal manipulation in all of the animals. Rarely, other changes such as focal increase in cellularity of the corneal stroma and a reduplication of Descemet's membrane were also noted in both the glyceraldehyde treated and saline treated groups. These changes were the consequence of overly aggressive corneal injection and not associated with treatment with the drops.

The results from this experiment indicate that the use of the 3% glyceraldehyde solution on rabbits produced no significant deleterious effects. Thus, the 3% glyceraldehyde solution may be used safely to facilitate reshaping corneal structure. Furthermore, the results taken from this experiment and from Examples 1 and 2 indicate that 3% glyceraldehyde treatment is safe.

Example 4 extends the above described results to a small scale safety study on the effects of 3% glyceraldehyde treatment in two non-sighted human patients.

EXAMPLE 4

The Safety of Enzymatic Corneaplasty with Hyaluronidase and Tonical Application of 3% Glyceraldehyde in Two Non-sighted Human Patients The two patients (Nos. 1108 and 1105) each received an intrastromal injection of 500 IU of hyaluronidase. The patients were observed for 20–28 days following the injection using methods similar to those described in Example 1. At the end of the observation period the patients were fitted with corrective lenses possessing a reverse geometric sculpture as described above, which they wore for an average of 8–12 hours/day. Patient 1108 wore the lenses for 21 days while patient 1105 wore the lenses for 50 days.

Patient 1108

Patient 1108 was treated according to the protocol outline above. After the 21 day lens wearing period had expired, the patient was instructed to apply two (2) drops of the 3% glyceraldehyde solution four times per day. The application of 3% glyceraldehyde continued for thirty-six (36) days after lens wear had ceased. Following termination of the 3% glyceraldehyde treatment, the patient was examined occasionally and the final examination was administered 126 days following the cessation of glyceraldehyde treatment.

Results from the observations taken of the patient indicate that patient 1108 manifested superficial punctate keratitis during RGP lens wear. However, since this condition had been seen previously in literature reports discussing the use of the RGP lenses, it is considered unlikely that the observations observed here were a result of the treatment protocol.

Observations of the patient did not indicate any deleterious effects on the stroma or the endothelial cells of this patient during the time period of the glyceraldehyde treatment. Nor were there any adverse reactions observed after completion of the 36 day treatment protocol, including at the time of the final examination.

Patient 1105

This patient was treated as described above and wore the RGP lenses for 50 days. Unlike patient 1108, patient 1105 was treated with the 3% glyceraldehyde solution for one (1) month while the patient was wearing the RGP contact lenses. The 3% glyceraldehyde solution was applied four times per day for a total period of 43 days.

During the period of lens wear, patient 1105 displayed signs of superficial punctate keratopathy (SPK) of the corneal epithelium. This condition likely arose from the wearing of the contact lenses. During the period of lens wear and 3% glyceraldehyde application, the level of SPK was not observed to increase. Thus application of the glyceraldehyde solution did not to serve to exacerbate the condition.

This conclusion is supported by the effect of lens removal on the observed SPK condition. Upon termination of lens wear while continuing the 3% glyceraldehyde treatment, the level of SPK was observed to decrease. Further, upon completion of the 43 day glyceraldehyde treatment protocol, within 48 hours of ceasing application of the glyceraldehyde solution, the corneas appeared normal under slit-lamp biomicroscopy and were free of any SPK. Similarly, the corneal epithelium, the stroma, and the endothelial cells of the treated eyes appeared normal.

In a follow-up examination of patient 1105 at 98 days post cessation of the glyceraldehyde treatment, the corneas of the patient appeared normal.

This initial study of two non-sighted human patients indicates that treatment of the human eye with a 3% glyceraldehyde solution produced no observable negative results. The SPK observed in the patients can be attributed to be a result of contact lens wear and not a result of glyceraldehyde treatment.

Based on these results the treatment of the present invention was considered safe. Studies consisting of larger test groups were pursued to emphasize this point and to investigate the safety of other embodiments of the present invention.

Example 5 describes a safety study involving five non-sighted patients who underwent non-enzyrnatic corneaplasty using corrective contact lenses and the application of a 3% glyceraldehyde solution.

EXAMPLE 5

The Safety of Non-Enzymatic Corneaplasty and Topical Application of 3% Glyceraldehyde in Five Non-sighted Human Patients In this study five non-sighted patients with good corneas were treated with contact lenses and a 3% glyceraldehyde solution to determine the safety of this procedure. Here, the patients were fitted with and wore contact lenses for seven (7) days. Following this period a 3% glyceraldehyde solution (described above) was applied to the eyes and the contact lens wear continued for twenty-eight (28) days. After this period both the contact lens wear and the glyceraldehyde treatment ceased.

The patients were individually examined for the effects of the treatments following removal of the lenses and cessation of the glyceraldehyde treatment. The first examination was on the last day of treatment, and five (5) subsequent examinations were administered over a one month period. Normal corneas were observed in all patients with only minor incidents of SPK reported.

| DAY | RESULTS |
|---|---|
| Patient 1203 | |
| Oct. 14, 1997 | Normal cornea with +1 SPK |
| Oct. 16, 1997 | Normal cornea, no SPK |
| Oct. 17, 1997 | Normal cornea, +1 SPK |
| Oct. 21, 1997 | Normal cornea |
| Nov. 10, 1997 | Normal cornea |
| Nov. 18, 1997 | Normal cornea |
| Patient 1208 | |
| Oct. 14, 1997 | Normal cornea |
| Oct. 16, 1997 | Normal cornea, +1 SPK |
| Oct. 17, 1997 | Normal cornea |
| Oct. 21, 1997 | Normal cornea, +1 SPK |
| Oct. 28, 1997 | Normal cornea |
| Nov. 10, 1997 | Normal cornea |
| Nov. 18, 1997 | Normal cornea with +1 SPK |
| Dec. 15, 1997 | Normal cornea |
| Patient 1211 | |
| Oct. 14, 1997 | Normal cornea with +1 SPK |
| Oct. 16, 1997 | Normal cornea with +1 SPK |
| Oct. 17, 1997 | Normal cornea |
| Oct. 21, 1997 | Normal cornea with +1 SPK |
| Oct. 28, 1997 | Normal cornea |
| Nov. 10, 1997 | Normal cornea |
| Nov. 18, 1997 | Normal cornea with ± SPK |
| Dec. 16, 1997 | Normal cornea |
| Patient 1212 | |
| Oct. 14, 1997 | Normal cornea |
| Oct. 16, 1997 | Normal cornea |
| Oct. 17, 1997 | Normal cornea |
| Oct. 21, 1997 | Normal cornea |
| Oct. 28, 1997 | Normal cornea |
| Nov. 10, 1997 | Normal cornea |
| Nov. 18, 1997 | Normal cornea |
| Dec. 16, 1997 | Normal cornea |
| Patient 1213 | |
| Oct. 14, 1997 | Normal cornea with +1 SPK |
| Oct. 16, 1997 | Normal cornea with +1 SPK |
| Oct. 17, 1997 | Normal cornea |
| Oct. 21, 1997 | Normal cornea with ±1 SPK |
| Oct. 28, 1997 | Normal cornea |
| Nov. 10, 1997 | Normal cornea |
| Nov. 18, 1997 | Normal cornea with +1 SPK |
| Dec. 16, 1997 | Normal cornea |

Score:
0 = Normal
+1 = A few spots of staining
+2 = Intermediate staining
+3 = Severe staining The results of this study further support the conclusion that 3% glyceraldehyde is safe to use in the eyes of human patients to facilitate the corneal structure alterations accomplished in the enzyme orthokeratology protocol of the present invention.

EXAMPLE 6

The Safety of Enzymatic Corneaplasty with Hyaluronidase and Topical Application of 3% Glyceraldehyde in Seven Non-sighted Human Patients The methodology used in this study was similar to that discussed in Example 4. Subjects were injected intrastromally with 500 IU of a hyaluronidase solution on the first day of the study following an initial eye examination. The injected enzyme was allowed to digest the corneal substrate for seven (7) days. At that time contact lenses were fitted to the treated eyes of the subjects. The subjects wore the lenses for another seven days at which time the topical application of the 3% glyceraldehyde solution was first applied. The 3% glyceraldehyde solution was applied at 2 drops, 4 times per day for the following 28 days. At the end of the 28 days the contact lenses were removed and the glyceraldehyde treatments were ceased.

The subjects were examined and data was recorded throughout the treatment period and following the cessation of treatment. Subject's eyes were monitored for changes in eye condition and that data is summarized below. As the data indicate, treated subjects showed no significant negative effects as a result of either enzyme injection or glyceraldehyde application. The only apparent negative effects of the treatment were incidents of edema and minor manifestations of SPK. These negative manifestations resolved favorably for most patients.

| DAY | RESULTS |
|---|---|
| Patient 1201 | |
| Sept. 9, 1997 | Normal cornea |
| Sept. 16, 1997 | Normal cornea, +1 Edema, +1 SPK |
| Sept. 23, 1997 | Normal cornea, +1 SPK |
| Sept. 30, 1997 | Normal cornea, +1 SPK |
| Oct. 7, 1997 | Normal cornea, +1 SPK |
| Oct. 16, 1997 | Normal cornea, +1 SPK |
| Oct. 28, 1997 | Normal cornea |
| Nov. 10, 1997 | Normal cornea |
| Dec. 16, 1997 | Normal cornea |
| Patient 1203 | |
| Sept. 9, 1997 | Normal cornea |
| Sept. 16, 1997 | Normal cornea, +1 SPK |
| Sept. 23, 1997 | Normal cornea, +1 SPK |
| Sept. 30, 1997 | Normal cornea, +1 SPK |
| Oct. 15, 1997 | Normal cornea, +1 SPK |
| Oct. 16, 1997 | Normal cornea |
| Oct. 18, 1997 | Normal cornea |
| Nov. 10, 1997 | Normal cornea |
| Nov. 18, 1997 | Normal cornea |
| Patient 1204 | |
| Sept. 9, 1997 | Normal cornea, +1 Edema |
| Sept. 16, 1997 | Normal cornea, +1 Edema, +1 SPK |
| Oct. 14, 1997 | Normal cornea, +1 SPK |
| Oct. 16, 1997 | Normal cornea, +1 SPK |
| Oct. 21, 1997 | Normal cornea, +1 SPK |
| Oct. 28, 1997 | Normal cornea, +1 SPK |
| Nov. 10, 1997 | Normal cornea, +1 SPK |
| Nov. 18, 1997 | Normal cornea, +1 SPK |
| Dec. 16, 1997 | Normal cornea, +1 SPK |
| Patient 1205 | |
| Sept. 9, 1997 | Normal cornea, +1 Precipitate |
| Sept. 16, 1997 | Normal cornea, +1 Ppt |
| Oct. 14, 1997 | Normal cornea, +1 Ppt, +1 SPK |
| Oct. 16, 1997 | Normal cornea, +1 Ppt |
| Oct. 21, 1997 | Normal cornea, +1 Ppt |
| Oct. 28, 1997 | Normal cornea, +1 Ppt |
| Nov. 10, 1997 | Normal cornea, +1 Ppt |
| Dec. 15, 1997 | Normal cornea, +1 Ppt |
| Patient 1206 | |
| Sept. 9, 1997 | Normal cornea, +1 Edema, +1 SPK |
| Sept. 16, 1997 | Normal cornea |
| Oct. 14, 1997 | Normal cornea, +1 SPK |
| Oct. 16, 1997 | Normal cornea, +1 SPK |
| Oct. 21, 1997 | Normal cornea, +1 SPK |
| Oct. 28, 1997 | Normal cornea, +1 SPK |
| Nov. 18, 1997 | Normal cornea, +1 SPK |

-continued

| DAY | RESULTS |
|---|---|
| | Patient 1209 |
| Sept. 9, 1997 | Normal cornea, +1 Edema |
| Sept. 16, 1997 | Normal cornea, +1 Edema, +1 SPK |
| Oct. 16, 1997 | Normal cornea, +1 SPK |
| Oct. 18, 1997 | Normal cornea, +1 SPK |
| | Patient 1210 |
| Sept. 9, 1997 | Normal cornea |
| Sept. 16, 1997 | Normal cornea, +1 SPK |
| Sept. 23, 1997 | Normal cornea, +1 SPK |
| Oct. 16, 1997 | Normal cornea, +1 SPK |
| Oct. 21, 1997 | Normal cornea, +1 SPK |
| Nov. 10, 1997 | Normal cornea, +1 SPK |
| Nov. 18, 1997 | Normal cornea, +1 SPK |
| Dec. 16, 1997 | Normal cornea |

Score:
0 = Normal
+1 = A few spots of staining
+2 = Intermediate staining
+3 = Severe staining The results of this study indicate that treatment of human eyes with 3% glyceraldehyde after intrastromal injection is also safe to use in the eyes of human patients to facilitate the corneal structure alterations accomplished in the enzyme orthokeratology protocol of the present invention.

EXAMPLE 7

Elasticity Measurements of Enzyme
Orthokeratology Treated Corneas

A precision spherical glass indentor was used to contact the corneal surface of subjects treated with the methods of the present invention to measure changes in corneal elasticity. The method used involved the application of the indentor, in the form of a small spherical ball to gently deflect into a test cornea to establish an initial deflection value. Measurements were taken by using an interferometer to view the deflection. Following this application, the relaxation period was measured by observing the change in the impression made by the indentor.

The indentation range of movement was characterized using a precision linear variable differential transducer (LVDT) device that measured the linear travel of a stage carrying the indentor probe. The average travel distance of the probe was established at approximately 700 micrometers. The contact depth of the indentor probe was measured by evaluating the corneal surface immediately after indentation and measuring the local height values caused by the probe contact. This value was measured to range from 266 to 300 micrometers.

The residual impression caused by the indentor was observed to diminish as a function of time. A digital timer was used to mark the beginning and ending times during observation. Changes in the impression were readily observed during this period. The final end point was considered to be when the local fringe disturbance was recovered blending with the undisturbed neighboring fringes. There is an acknowledged component of subjective evaluation error contained within these results. However, given the time scales involved, the value of this error is considered to be small.

For example, a hyaluronidase treated eye was observed to take thirty (30) minutes or longer to recover from indentation as compared to a normal eye which was observed to recover in two (2) minutes. This large difference in values makes the subjective nature of the observations tolerable.

The method of inducing corneal inflection involved first contacting the test corneal with the indentor. After the initial contact with the cornea was established, the probe was moved forward into the cornea to a predetermined distance. Seven hundred microns was used to achieve adequate deflection. Topography was taken immediately after the deflection to record the impression made in the cornea. Observations of the cornea were then made at one (1) minute intervals to note the change in the impression made. This proved to be quite valuable in noting the elastic response of the cornea subsequent to impression. Another topography was done after five (5) minutes to record the final condition of the impression. These measurements were taken to establish a baseline elasticity and to determine the effect of various Enzyme Orthokeratology treatments on corneal elasticity.

Measurements taken indicate that eyes injected with the hyaluronidase solution of the present invention undergo a significant reduction in corneal elasticity as compared to baseline measurements. Comparing the time required for a cornea to recover from an impression made using the indentor probe, hyaluronidase treated eyes take much longer to recover than the untreated eye. The normal, untreated cornea recovers from the impression within 1–3 minutes, while the hyaluronidase treated eye takes 6–30 minutes or longer to recover, depending on the age of the patient. These results indicate that treatment of a cornea with a corneal softening agent like hyaluronidase reduces corneal elasticity.

Conversely, treatment of a cornea with a corneal hardening agent results in an increase in corneal elasticity. Using the present assay method, the elasticity of test eyes was measured before and after treatment with the glyceraldehyde solution of the present invention. After glyceraldehyde treatment the corneas became more elastic, as determined from the more rapid time of indentation recovery. The recovery curve changed with continued application of the solution in drop form over a two week period. After about two weeks glyceraldehyde treated patients displayed a recovery time of within 20–30 seconds. Interestingly, these patients showed little change in elasticity after this point but maintained the observed rapid recovery times.

The results from this study indicate that the Enzyme Orthokeratology methods of the present invention are effective in altering the rigidity or elasticity of the cornea. The results also show that application of the corneal hardening agent of the present invention induces corneal rigidity.

EXAMPLE 8

The Safety And Efficacy Of Hyaluronidase And
Topical 3% Glyceraldehyde Solution Treatment Of
Myopia In A Human Patient In this study, a single subject was selected to test the safety and efficacy of using hyaluronidase and a glyceraldehyde solution to treat sub-optimal visual acuity. In this study, the subject was first medically evaluated and a baseline was established. A medical history of the subject was taken and a detailed examination of the subject's eyes was also performed. The subject's eyes were tested to determine: refraction, cell count, intraocular pressure (IOP), pachymetry, corneal topography and corneal elasticity. A slit-lamp examination was also performed to establish the health of the eyes. Also, the presence of any general or ocular discomfort of the subject was noted.

Following the establishment of a baseline reading (UVA 20/300), the subject was administered a single intrastromal injection of 50 IU hyaluronidase prior to the orthokeratology treatment. Following 7 days of incubation of the subject's eyes with the injected material, the subject was fitted with corrective contact lenses for overnight wear. The subject wore the corrective lenses day and night for a period of seven (7) days. At this point the subject's visual acuity was 20/15. After seven days of corrective lens wear (May 11, 1998), the subject began receiving an application of the topical 3% glyceraldehyde solution ophthalmic drops four times per day (08:00, 12:00, 16:00, and 20:00) for 15 days, in conjunction with daytime lens wear for stabilization. After 15 days, the lens wear and drops were discontinued. The visual acuity of the subject was then monitored for 196 days to determine the effect of the treatment on the unaided visual acuity of the subject;

As is apparent from Table I, the unaided visual acuity of the subject retained its improved state long after the support lens was removed. In fact, the results in Table I clearly indicate that the combined administration of hyaluronidase and the glyceraldehyde solution of the present invention, in conjunction with corneaplasty, were effective in correcting the unaided visual acuity of the patient for more than six months. These results clearly indicate the effectiveness of the methods of the present invention.

TABLE I

Corneaplasty Procedure with Patient No. CG08 - OD Treated 50 I.U.

| Date | Treatment Description | Slit Lamp Biomicroscopy | Aided VA Refraction | Unaided VA Refraction | I.O.P. | Corneal Thickness |
|---|---|---|---|---|---|---|
| Apr. 20, 1998 | Baseline | Rose Bengal + 1 Haze + 1 | −3.00–0.50 20/20 | −3.00–1.00 20/300 | 15 mm | 0.562 |
| Apr. 28, 1998 | PHH 03-05 Inj. HYA | — | — | — | — | — |
| Apr. 29, 1998 | 1 Day Post Injection | C. Edema + 1 Flare + 1 | — | — | — | — |
| Apr. 30, 1998 | 2 Days P.I. | C. Edema + 1 Haze + 1 | −3.25–0.50 20/20 | 20/50 | — | 0.500 |
| May 4, 1998 | 6 Days P.I. | C. Edema + 1 | −3.00–1.00 20/20 | 20/200 | — | 0.485 |
| May 5, 1998 | 7 Days P.I. Lens On | 0 | −2.25 Sph. 20/20 | 20/50 | — | 0.483 |
| May 6, 1998 | 1 Days @ Lens | SPK + 1 | Plano 20/20 | 20/20 | 10 mm | 0.471 |
| May 7, 1998 | 2 Days @ Lens | SPK + 1 | Plano 20/15 | 20/15 | 10 mm | 0.473 |
| May 8, 1998 | 3 Days @ Lens | SPK + 1 | Plano-0.50 20/15 | 20/15 | 10 mm | — |
| May 9, 1998 | 4 Days @ Lens | 0 | Plano 20/15 | 20/15 | 10 mm | — |
| May 11, 1998 | 7 Days @ Lens Start Drops | 0 | Plano 20/15 | 20/15 | 10 mm | 0.470 |
| May 12, 1998 | 1 Day @ Drops | 0 | Plano 20/15 | 20/15 | 11 mm | 0.476 |
| May 13, 1998 | 3 Days @ Drops | 0 | −1.00–0.75 20/15 | 20/40 | — | 0.475 |
| May 14, 1998 | 4 Days @ Drops | 0 | Plano 20/15 | 20/15 | — | 0.462 |
| May 15, 1998 | 5 Days @ Drops | SPK + 1 | Plano 20/15 | 20/15 | 11 mm | 0.475 |
| May 18, 1998 | 7 Days @ Drops | SPK + 1 | Plano 20/15 | 20/15 | 10 mm | 0.476 |
| May 19, 1998 | 8 Days @ Drops | SPK + 1 | Plano 20/15 | 20/15 | 11 mm | — |
| May 20, 1998 | 9 Days @ Drops | 0 | 0.25 Sph. 20/15 | 20/20 | 11 mm | 0.475 |
| May 21, 1998 | 10 Days | 0 | Plano 20/15 | 20/15 | 10 mm | 0.474 |
| May 22, 1998 | 11 Days | SPK + 1 | Plano 20/25 | 20/25 | 11 mm | 0.473 |
| May 25, 1998 | 14 Days | SPK + 1 | Plano-0.50 20/15 | 20/20 | — | 0.464 |
| May 26, 1998 | Lens & Drops 15 Days-Stop | SPK + 1 | −0.50 Sph. 20/15 | 20/15 | 11 mm | 0.477 |
| May 28, 1998 | No Lens No Drops, 2 days | 0 | −1.75–0.75 20/15 | 20/50 | 14 mm | 0.481 |
| June 2, 1998 | 7 Days | 0 | −2.00–0.50 20/15 | 20/200 | 10 mm | 0.492 |
| June 4, 1998 | 9 Days | 0 | −2.50–0.50 20/15 | 20/70 | — | — |
| June 9, 1998 | 14 Days | 0 | −2.25-Sph. 20/15 | 20/50 | 11 mm | 0.484 |
| June 16, 1998 | 21 Days | 0 | −2.50–0.50 20/15 | 20/40 | 12 mm | 0.500 |

TABLE I-continued

Corneaplasty Procedure
with
Patient No. CG08 - OD Treated 50 I.U.

| Date | Treatment Description | Slit Lamp Biomicroscopy | Aided VA Refraction | Unaided VA Refraction | I.O.P. | Corneal Thickness |
|---|---|---|---|---|---|---|
| June 23, 1998 | 28 Days | 0 | −1.25−0.75 20/20 | 20/30 | — | 0.506 |
| June 30, 1998 | 35 Days | SPK + 1 | −1.25−1.25 20/15 | −20/30 | 10 mm | 0.496 |
| July 7, 1998 | 42 Days | SPK + 1 | −1.50−1.00 20/20 | 20/30 | 10 mm | 0.504 |
| July 14, 1998 | 49 Days | 0 | −0.75−1.00 20/20 | 20/25 | 12 mm | 0.500 |
| July 22, 1998 | 59 Days | 0 | Plano 20/20 | 20/20 | 10 mm | 0.507 |
| July 28, 1998 | 65 Days | 0 | −0.50 Sph. 20/20 | 20/15 | 12 mm | 0.508 |
| Aug. 6, 1998 | 74 Days | 0 | −1.00 Sph. 20/20 | 20/25 | 12 mm | 0.500 |
| Aug. 18, 1998 | 87 Days | 0 | −1.00 Sph. 20/15 | 20/25 | 14 mm | 0.516 |
| Aug. 26, 1998 | 94 Days | 0 | Plano-0.75 20/20 | 20/25 | 12 mm | 0.506 |
| Sept. 1, 1998 | 102 Days | 0 | Plano 1.00 20/20 | 20/25 | 14 mm | 0.465 |
| Sept. 8, 1998 | 109 Days | 0 | +0.50 0.75 20/20 | 20/25 | 12 mm | 0.525 |
| Sept. 15, 1998 | 117 Days | 0 | +0.50 Sph. 20/20 | 20/20 | 14 mm | 0.527 |
| Sept. 22, 1998 | 124 Days | 0 | −0.50−0.50 20/20 | 20/20 | 12 mm | 0.530 |
| Oct. 6, 1998 | 138 Days | 0 | −0.75−1.00 20/20 | 20/20 | 12 mm | 0.528 |
| Oct. 13, 1998 | 145 Days | 0 | Plano 20/20 | 20/20 | 10 mm | 0.524 |
| Oct. 20, 1998 | 152 Days | 0 | Plano 20/20 | 20/20 | 14 mm | 0.532 |
| Oct. 26, 1998 | 158 Days | 0 | −1.25−0.50 20/20 | 20/25 | — | — |
| Nov. 2, 1998 | 165 Days | 0 | Plano-0.50 20/20 | 20/20 | — | 0.536 |
| Nov. 10, 1998 | 173 Days | 0 | Plano 20/20 | 20/20 | 14 mm | 0.539 |
| Nov. 17, 1998 | 180 Days | 0 | Plano 20/15 | 20/15 | 14 mm | 0.543 |
| Nov. 25, 1998 | 188 Days | 0 | Plano 20/20 | 20/20 | 14 mm | 0.539 |
| Dec. 3, 1998 | 196 Days | 0 | Plano-0.50 20/20 | 20/20 | 0 | 0.553 |

EXAMPLE 9

The Safety and Efficacy of Hyaluronidase and Topical 3% Glyceraldehyde Solution Treatment of Mild Myopia in Human Patients Given the favorable results obtained in Example 8, an additional study was undertaken to test the safety and efficacy of the method of the present invention using a larger group of subjects. In this study, a group of subjects were selected and randomly separated into three test groups to test the safety and efficacy of using hyaluronidase and a glyceraldehyde solution for treating subjects with sub-optimal visual acuity. Groups one and two received an intrastromal injection of hyaluronidase (50 and 500 IU, respectively), while group three received a control injection of saline.

Following a two week incubation period after the injection, the three groups were fitted with corrective lenses to optimize the visual acuity of the subjects. The corrective lenses were left in place for a period of time sufficient to alter the shape of the subjects' eyes so as to achieve an optimal visual acuity. This period of time was generally 2 days in length. Once an acceptable visual acuity was achieved, the subjects in the three groups received a topical 3% glyceraldehyde solution in the form of ophthalmic drops four times per day while wearing the corrective lenses. The glyceraldehyde treatment was generally administered for one month. Lens wear occurred from 8 to 12 hours during the day.

At the end of the treatment period both the lens wear and the glyceraldehyde solution administration was terminated. The general health and visual acuity of the subjects was monitored from 3 to 5 months following treatment termination. The results of this study are reported below.

Subject Criteria

To participate in this study, a subject must manifest myopia requiring less than 2 diopters of correction and astigmatism requiring less than 1 diopter of correction. In addition, a subject must be 18 years of age or older who has the capacity to give informed consent by reading and signing an Informed Consent Form that describes the present study and its attendant risks. Subjects must also be willing to participate in all examinations scheduled. Finally, the subjects must be female and post-menopausal, sterilized, using an effective form of birth control, or otherwise unable to bear children. Male subjects are also acceptable.

Subjects were excluded from the study if they are participating in another research study or were hypersensitive to the study medication or study reagents. Subjects with ongoing corneal abnormalities that would preclude an accurate reading with an applanation tonometer or a tonopen and subjects with ongoing ocular infection, inflammation, or a history of herpetic corneal lesions which have cleared within one month or less, prior to the study, were also be excluded.

Subjects were permitted take systemic medications that were considered necessary for the subject's welfare and that would not interfere with the study. Also, systemic and/or topical anti-inflammatories, antibiotics, and/or cycloplegics to treat or assess the ocular conditions were available for use at the discretion of the investigator. Use of all such drugs, if any, were reported to the study administrator.

Subjects that qualified for the study based on the criteria described above and who agreed to participate were randomized into one of three groups and then treated according to the protocols of their individual groups.

First Group: Corrective Lenses and 3% Glyceraldehyde Solution

Before beginning the experimental protocol, test subjects were examined initially to establish a baseline from which the future results of the treatment were compared. For each subject a medical history was taken and a detailed examination of the eyes was also performed. The eyes of each subject were tested to determine: refraction cell count, intraocular pressure (IOP), pachymetry, corneal topography and corneal elasticity. A slit-lamp examination was also performed to establish the health of the eye. Also, the presence of any general or ocular discomfort of the subjects was noted.

Following the establishment of a baseline reading, group 1 subjects were administered a single intrastromal injection of 50 IU hyaluronidase prior to the orthokeratology treatment. Following 14 days of incubation, the subjects were fitted with corrective contact lenses for overnight wear. Subjects wore the corrective lenses night and day for a period of two (2) to seven (7) days or until visual 20/20 visual acuity was achieved. Subjects achieving an acceptable visual acuity (approximately 20/20) received an application of the topical 3% glyceraldehyde solution ophthalmic drops four times per day (8:00, 12:00, 16:00, and 20:00) for a period of 1 month in conjunction with daytime lens wear for stabilization. Lens wear lasted for 8 to 12 hours per day. The subjects were examined periodically during the glyceraldehyde treatment to monitor changes in the health of the treated eyes. All of the examinations described above were performed during each visit except the medical history, which did not require repetition, and the cell count, which was not performed again until the terminal period of the study.

At the end of the treatment period, the stabilizing lens were removed and the administration of the 3% glyceraldehyde solution was terminated. Following termination of the treatment, the subjects were examined immediately after treatment was terminated, once a week for the first four weeks after termination, and then monthly to measure changes in the visual acuity of the treated eyes. The health of the eye was also monitored. Sequelae characterized by the appearance or worsening of serious ocular symptoms or slit-lamp findings observed during these examinations was assessed. The proportions of subjects with such findings were analyzed.

The time course of visual acuity correction retention for this group are shown in Table II: The baseline visual acuity of the subjects ranged from a low of 20/63 in one subject's eyes (OCS/022R) to a high of 20/300. All members of the group achieved an acceptable level of correction to their visual acuity (20/20 in all subjects except ARR/001: 20/25 and JLV/015: 20/40). These results show that all subjects responded to the initial orthokeratological treatment.

Over the course of the monitoring period, each subject maintained a degree of the initial correction in visual acuity as compared to baseline. The retention in correction was mediated by the orthokeratological treatment. Visual acuity measurements for the subjects are shown in Table II. Examining the subjects in order of length of monitoring, ARR/001 had a baseline measurement of 20/80 and was measured at 20/40 at the 5-month follow up. JCV/002 had a baseline of 20/300 and measured 20/125 at the 4-month follow-up. At the 3-month follow-up point, SRA/007 had a visual acuity of 20/50, FAH/009 had a visual acuity of 20/63, and JLV/015 had a visual acuity of 20/25. Comparing these results to these subject's baseline measurements of 20/200, 20/200, and 20/80, respectively, shows that the use of hyaluronidase, corrective lenses and the glyceraldehyde solution of the present invention acted to correct the visual acuity of these subjects.

Similarly, comparing the visual acuity measurements for other subjects who have not yet completed the treatment protocol shows that the methods of the present invention are effective to correct the visual acuity of the test subjects. For example, at the 2-month point, LMR/028 had a visual acuity of 20/125, down from a baseline of 20/300; GJM/029 had a visual acuity of 20/40, down from a baseline of 20/200; and ECF/033 had a visual acuity of 20/125, an improvement over the baseline of 20/300. Subjects JRF/010R and JLM/024R changed from 20/80 and 20/100, respectively, to 20/20 and 20/40, respectively. Only OCS/022R failed to show an improvement over the baseline measurement of 20/62 since this subject measured 20/80 at the 3-week followup. Nevertheless, given the early state of data collection from this individual, it is possible, and even likely in view of the results obtained for the other subjects, that the measurements for OCS/022R will improve.

The results shown in Table II indicate that glyceraldehyde treatment of a subjects' eyes in conjunction with the injection of 50 IU of hyaluronidase was effective in facilitating the correction of the subjects' visual acuity.

Group II: 500 IU Hyaluronidase Injection, Corrective Lenses and 3% Glyceraldehyde Solution The subjects of group II were treated as those in group I in preparation for their participation in the study reported here. Before beginning the experimental protocol, test subjects were examined initially to establish a baseline from which the future results of the treatment were compared.

Following the establishment of a baseline reading, group II subjects were fitted with contact lenses and wore the corrective lenses at night for a period of two (2) to seven (7) days or until an acceptable visual acuity (approximately 20/20) was achieved. Group II test subjects received 500 IU of hyaluronidase by injection as compared to the 50 IU of group I. Two groups of subjects received 500 IU of hyaluronidase. The results obtained from the first group are shown in Table IIIA and the results from the second group are shown in Table IIIA and are identified in the table by the notation Gr. VI. There were no meaningful differences in the treatment protocols between these two groups. Subjects achieving an acceptable visual acuity received the topical 3% glyceraldehyde solution in the form of ophthalmic drops four times per day (08:00, 12:00, 16:00, and 20:00) for a period of 1 month in conjunction with daytime lens wear for stabilization. During this period, lens were occurred for approximately 8–12 hours per day and there was no nocturnal lens wear.

The subjects were examined periodically during the glyceraldehyde treatment to monitor changes in the health of the treated eyes. All of the examinations described above were performed during each visit except the medical history, which did not require repetition, and the cell count, which was not performed again until the terminal period of the study.

At the end of the treatment period, the stabilizing lens were removed and the administration of the 3% glyceraldehyde solution was terminated. Following termination of the treatment, the subjects were examined immediately after treatment was terminated, once a week for the first four weeks after termination, and then monthly to measure changes in the visual acuity of the treated eyes. The health of the eye was also monitored. Sequelae characterized by the appearance or worsening of serious ocular symptoms or slit-lamp findings observed during these examinations were assessed. The proportions of subjects with such findings were analyzed.

The visual acuity data for this group are shown in Tables IIIA and IIIB. The table values shown are the better values as compared between the results of the two methods. The subjects' baseline visual acuity ranged from 20/50 to 20/500 in Table IIIA and 20/60 to 20/400 in Table IIB. All members of the group achieved an acceptable visual correction to their visual acuity ranging from 20/12.5 to 20/20 with subject YAM/013 measuring at 20/40 in Table IIIA and 20/15 to 20/25 with subject LMR/104 measuring at 20/50.

The visual acuity of each subject was monitored and tabulated to observe the degree of correction maintained by the treated subjects after the corrective lenses were removed. Generally, all of the subjects retained at least a portion of the improvement over the baseline mediated by the orthokeratological treatment.

At the four month point, subject ECS/004 had a UVA of 20/50, a marked improvement over the subject's baseline of 20/160. At the three month point, subject P10/008 had a UVA of 20/80 as compared to a baseline measurement of 20/400; subject YAM/013 had a UVA of 20/40 as compared to a baseline measurement of 20/100; subject YOC/017 has a UVA of 20/25 from a baseline of 20/50; subject FGM/018 had a UVA of 20/25 as compared to a baseline of 20/80; subject JPG/019 had a UVA of 20/15 as compared to a baseline of 20/70; and subject OOS/031 had a UVA of 20/50 as compared to a baseline of 20/200.

Results from the two month time point were similar to the three month results. For example, subject FMP/023 had a UVA at two months of 20/20 as compared to a baseline of 20/70; subject ERG/026 had a UVA of 20/25 as compared to a UVA of 20/50 baseline; and subject ELG/030 had a UVA of 20/100 as compared to the baseline measurement of 20/300.

The results shown in Table IIIB also show the effectiveness of the treatment. At the two month date, subjects treated with 500 IU of hyaluronidase (Gr. VI) showed marked improvement over their baseline measurements. For example, at the two month date, subject AVM/102 had a UVA of 20/20 an improvement over the baseline UVA of 20/160; LLG/103 had a UVA of 20/50 as compared to a baseline UVA of 20/160; subject IEV/105 had a UVA of 20/80 as compared to a baseline of 20/200; and subject GVC/106 had a UVA of 20/63 as compared to a baseline of 20/160. At the one month time point, subject NMD/101 had a WVA of 20/60 as compared to a baseline measurement of 20/200; subject LMR/104 had a UVA 20/80 as compared to a baseline measurement of 20/200; finally, subject MCS/107 had a UVA of 20/20 as compared to a baseline measurement of 20/60.

The results shown in Tables IIIA and IIIB indicate that a combination of hyaluronidase and glyceraldehyde treatment of a subject's eyes is effective at retaining the benefits of orthokeratology long after the subject has ceased to wear the corrective lens.

Group III: Corrective Lenses and 3% Glyceraldehyde Solution Treatment in the Absence of Hyaluronidase As with groups I and II, the test subjects were examined initially to establish a baseline from which the future results of the treatment were compared. Following the establishment of a baseline reading, group III subjects were fitted with contact lenses and wore the corrective lenses at night for a period of two (2) to seven (7) days or until an acceptable visual acuity (approximately 20/20) was achieved. Unlike groups I and II, group III test subjects in this group received no injection of hyaluronidase during the course of treatment. Subjects achieving an acceptable visual acuity received the topical 3% glyceraldehyde solution in the form of ophthalmic drops four times per day (08:00, 12:00, 16:00, and 20:00) for a period of 1 month in conjunction with daytime lens wear for stabilization. During this period, lens wear occurred for approximately 8–12 hours per day and there was no nocturnal lens wear.

The subjects were examined periodically during the glyceraldehyde treatment to monitor changes in the health of the treated eyes. All of the examinations described above were performed during each visit except the medical history, which did not require repetition, and the cell count, which was not performed again until the terminal period of the study.

At the end of the treatment period, the stabilizing lens were removed and the administration of the 3% glyceraldehyde solution was terminated. Following termination of the treatment, the subjects were examined immediately after treatment was terminated, once a week for the first four weeks after termination, and then monthly to measure changes in the visual acuity of the treated eyes. The health of the eye was also monitored. Sequelae characterized by the appearance or worsening of serious ocular symptoms or slit-lamp findings observed during these examinations was assessed. The proportions of subjects with such findings were analyzed.

The visual acuity data for this group is shown in Table IV. The visual acuity values shown are obtained using the Snellen letters test and the Early Treatment Diabetic Retinopathy Study (ETDRS) protocol. The table values shown are the better values as compared between the results of the two methods. The subjects' baseline visual acuity ranged from 20/80 to 20/300. All members of the group achieved an acceptable correction to their visual acuity ranging from 20/12.5 to 20/20 in all but one subject.

Over the course of the next three or more months, each subject maintained a degree of the initial correction in visual acuity over baseline mediated by the orthokeratological treatment. At the five month time point, subject GVC/006 had a UVA of 20/100 as compared to a baseline UVA of 20/200. Three subjects measured at the four month time point ESV/005, JAM/012, and MCS/016 have UVAs of 20/100, 20/100 and 20/80, respectively. The baseline for these subjects were 20/100, 20/200, and 20/300, respectively. The greatest improvements retained at the three month follow-up time point were in subjects SGS/011, MCS/016, and AJG/014. SGS/011 started the study with a baseline of 20/20 and showed a visual acuity of 20/40 at the three month follow-up point. Subject MCS/016 started the study with a visual acuity of 20/300 and was measured at the three month point at 20/60. Subject AJG/014 had a baseline of 20/80 and was measured at the three month time point at 20/50.

Subjects ERR/021 and ARP/032 only have progressed through two months of the study. These subjects had UVAs of 20/60 each at the two month time point. Their respective baseline measurements were 20/80 and 20/120.

The results shown in Table IV indicate that glyceraldehyde treatment of a subjects' eyes is effective in extending the retention time for the benefits accrued from a course of orthokeratology treatment, even in the absence of hyaluronidase.

Although this invention has been described in terms of certain embodiments, these embodiments are set forth for illustrative purposes and are not intended to limit the scope of the invention. It is apparent to those skilled in the art that various other modifications may be made to these embodiments without departing from the scope of the invention, which is properly determined upon reference to the following claims.

What is claimed is:

1. A method of correcting refractive errors in an eye of a subject mammal, comprising:

selecting a pharmaceutically acceptable corneal hardening agent on the basis of its being able to harden the cornea in said eye of said subject mammal without causing damage to said cornea;

administering to said eye of said subject mammal a corneal hardening amount of said agent so that said cornea can be reshaped from a first configuration to a desired second configuration;

fitting said cornea with a rigid contact lens having a concave curvature of said desired second configuration;

permitting said cornea to reshape to said desired second configuration under the influence of said lens; and removing said lens when said cornea is capable of maintaining said desired second configuration without the support of said lens; wherein said corneal hardening agent is glyceraldehyde.

2. The method of claim 1, wherein said refractive error is selected from the group consisting of myopia, hyperopia and astigmatism.

3. The method of claim 1, wherein said agent is administered by injection into the eye.

4. The method of claim 1, wherein said agent is administered by topical administration into the eye in the form of eye drops.

5. The method of claim 1, wherein said agent is administered by means of said contact lens.

6. The method of claim 1, further comprising the step of administering to said eye a corneal softening amount of a pharmaceutically acceptable corneal softening agent sufficient to soften the cornea of said eye so that said cornea can be reshaped.

7. The method of claim 6, wherein said corneal softening agent is an enzyme that degrades proteoglycans in said cornea.

8. The method of claim 7, wherein said proteoglycan degrading enzyme is hyaluronidase.

* * * * *